(12) United States Patent
Singh et al.

(10) Patent No.: US 11,589,747 B2
(45) Date of Patent: Feb. 28, 2023

(54) WIRELESS BIOLOGICAL MONITORING

(71) Applicants: Rahul Singh, Encinitas, CA (US); Peter John Bonin, III, Santa Ana, CA (US); Martin Oliver Culjat, San Diego, CA (US); Richard Brand Caso, Mission Viejo, CA (US)

(72) Inventors: Rahul Singh, Encinitas, CA (US); Peter John Bonin, III, Santa Ana, CA (US); Martin Oliver Culjat, San Diego, CA (US); Richard Brand Caso, Mission Viejo, CA (US)

(73) Assignee: Mothership Medical, Inc., Vista, CA (US)

( * ) Notice: Subject to any disclaimer, the term of this patent is extended or adjusted under 35 U.S.C. 154(b) by 0 days.

(21) Appl. No.: 17/227,754

(22) Filed: Apr. 12, 2021

(65) Prior Publication Data

US 2021/0228076 A1 Jul. 29, 2021

Related U.S. Application Data

(62) Division of application No. 15/911,357, filed on Mar. 5, 2018, now Pat. No. 11,006,831.

(51) Int. Cl.
*A61B 5/00* (2006.01)
*H04W 4/38* (2018.01)
(Continued)

(52) U.S. Cl.
CPC .......... *A61B 5/002* (2013.01); *A61B 5/02411* (2013.01); *A61B 5/033* (2013.01);
(Continued)

(58) Field of Classification Search
CPC ....... A61B 5/002; A61B 5/4356; A61B 5/742; A61B 8/02; A61B 8/4416; A61B 8/4472;
(Continued)

(56) References Cited

U.S. PATENT DOCUMENTS 5,373,852 A * 12/1994 Harrison .............. A61B 5/0002
128/903
5,862,803 A 1/1999 Besson et al.
(Continued)

*Primary Examiner* — Hongmin Fan
(74) *Attorney, Agent, or Firm* — Sunstein LLP

(57) ABSTRACT

A patient monitoring system includes: a biomedical sensor including: a transducer configured to produce a signal corresponding to a biological function; a sensor converter configured to convert the signal to a converted signal; and a transmitter configured to produce a communication, based on the converted signal, that is indicative of one or more values of the biological function, and to send the communication wirelessly; and a base station including: a receiver configured to receive the communication wirelessly and to produce a receiver output signal; a base station interface configured to produce a base station output signal indicative of the one or more values of the biological function; and at least one output port to receive the base station output signal and configured to be hard-wire connected to a display that is configured to display information indicative of the biological function.

4 Claims, 13 Drawing Sheets

(51) Int. Cl.
   *H04L 67/12*   (2022.01)
   *A61B 8/02*   (2006.01)
   *A61B 8/00*   (2006.01)
   *A61B 8/08*   (2006.01)
   *A61B 5/024*   (2006.01)
   *A61B 5/03*   (2006.01)
   *A61B 5/24*   (2021.01)

(52) U.S. Cl.
   CPC .............. *A61B 5/24* (2021.01); *A61B 5/4356* (2013.01); *A61B 5/6831* (2013.01); *A61B 5/742* (2013.01); *A61B 8/02* (2013.01); *A61B 8/08* (2013.01); *A61B 8/0883* (2013.01); *A61B 8/4227* (2013.01); *A61B 8/4416* (2013.01); *A61B 8/4427* (2013.01); *A61B 8/4472* (2013.01); *A61B 8/4488* (2013.01); *A61B 8/488* (2013.01); *A61B 8/5207* (2013.01); *A61B 8/5223* (2013.01); *A61B 8/56* (2013.01); *A61B 8/565* (2013.01); *A61B 8/58* (2013.01); *H04L 67/12* (2013.01); *H04W 4/38* (2018.02); *A61B 8/0866* (2013.01); *A61B 8/4411* (2013.01); *A61B 8/4433* (2013.01); *A61B 2560/0214* (2013.01); *A61B 2560/0223* (2013.01); *A61B 2562/0261* (2013.01)

(58) Field of Classification Search
   CPC ......... A61B 8/488; A61B 8/56; A61B 8/0866; A61B 2560/0214; A61B 2560/0223; A61B 2562/0261; H04L 67/12; H04W 4/38

See application file for complete search history.

(56) References Cited

U.S. PATENT DOCUMENTS

| | | |
|---|---|---|
| 6,117,086 A | 9/2000 | Shulze |
| 6,238,338 B1 | 5/2001 | DeLuca et al. |
| 2005/0267377 A1* | 12/2005 | Marossero .............. A61B 5/391 128/920 |
| 2006/0094936 A1 | 5/2006 | Russ |
| 2006/0258929 A1 | 11/2006 | Goode, Jr. et al. |
| 2008/0177154 A1* | 7/2008 | Hansen ................... A61B 5/157 600/300 |
| 2009/0299212 A1* | 12/2009 | Principe ................. A61B 5/391 600/588 |
| 2011/0077522 A1 | 3/2011 | Sato |
| 2011/0301439 A1 | 12/2011 | Albert et al. |
| 2012/0212582 A1 | 8/2012 | Deutsch |
| 2012/0232398 A1 | 9/2012 | Roham et al. |
| 2013/0134989 A1 | 5/2013 | Cloutier et al. |
| 2013/0261464 A1 | 10/2013 | Singh et al. |
| 2016/0331299 A1* | 11/2016 | Cline ..................... A61B 5/721 |
| 2017/0281087 A1* | 10/2017 | Workman ........... A61B 5/02411 |

\* cited by examiner

WIRELESS BIOLOGICAL MONITORING

CROSS-REFERENCE TO RELATED APPLICATIONS

This application is a divisional of application Ser. No. 15/911,357 filed Mar. 5, 2018, entitled "WIRELESS BIOLOGICAL MONITORING," which is assigned to the assignee hereof and is incorporated herein by reference.

BACKGROUND

It is often desirable to monitor a patient and/or an in utero child before and during labor and delivery. For example, it may be desirable to monitor the patient's uterine contractions and/or to monitor a heartbeat of the child. Monitoring of uterine contractions and fetal heartbeat is known as cardiotocography (CTG). CTG systems typically use Doppler ultrasound analysis to monitor the fetal heartbeat and a tocodynamometer (TOCO) transducer to monitor uterine contraction duration and possibly intensity.

Referring to FIG. 1, a prior art wired patient monitoring system 500 includes a sensor pack 502, and a monitor 504. The sensor pack 502 is attached to a patient 506 by a strap 508 and is hard-wired to the monitor 504 by a wire 510. The patient wears the strap 508 around the patient's abdomen, with the strap having the sensor unit 502 connected to the strap 508. The sensor unit 502 includes an ultrasound transducer for monitoring the fetal heartbeat and a TOCO transducer for monitoring uterine contractions. The ultrasound transducer and TOCO transducer are connected to the monitor 504 that contains signal processing electronics and a display 512 that provide diagnostic and monitoring information related to the labor, including values corresponding to uterine contraction (e.g., duration, magnitude) and values corresponding to a fetal heartbeat (e.g., rate, magnitude of heart contraction). The ultrasound and TOCO transducers are connected to the monitor 504 by one or more cables and connectors, here represented by the wire 510 and a connector 514. The hard-wire connection inhibits the patient's mobility, requiring disconnection of the CTG system to permit the patient 506 to move, e.g., to walk around as is recommended for patients in labor. While for simplicity and ease of illustration, the sensor pack 502 shown in FIG. 1 includes the ultrasound transducer and the TOCO transducer, the ultrasound transducer and the TOCO transducer may be physically separate devices, e.g., contained in physically separate housings, attached to the patient with separate straps, and wired to the monitor 504 with separate wires (and possibly multiple wires corresponding to each transducer).

Referring also to FIG. 2, the sensor unit 502 of the system 500 includes a wired TOCO transducer 520 and a wired ultrasound transducer 522. The TOCO transducer 520 includes two strain gauges 524, 526 that provide resistances 532, 534 of a Wheatstone bridge 530, with two other resistors 536, 538 of the bridge 530 being fixed. The strain gauges 524, 526 are disposed on respective sides of a material 540, e.g., a piece of metal, and are configured to measure deflection of respective sides of the material 540 and provide resistance values for the resistors 532, 534 corresponding to the deflection. Reference voltages V+ and V− are applied to top and bottom nodes of the bridge 530 and side nodes of the bridge 530 provide Defl+ and Defl− voltages indicative of the deflection of the material 540, and thus indicative of a uterine contraction. A magnitude difference of the deflection voltages Defl+ and Defl− is indicative of a magnitude of the contraction, and a time period over which the deflection voltages Defl+ and Defl− have a non-zero difference corresponds to a duration of the contraction. The references voltages V+ and V− and the deflection voltages Defl+ and Defl− are provided on respective wires to the wired monitor 504.

The wired ultrasound transducer 522 includes a piezoelectric element 550, a front electrode 552, and a back electrode 554. The electrodes 552, 554 may be excited to induce an outbound ultrasound signal 556. The outbound ultrasound signal 556 will reflect off of a fetal heart and return as an inbound ultrasound signal 558 that has been Doppler shifted due to motion of the heart. The inbound ultrasound signal will cause the piezoelectric element to vibrate, thereby inducing a Transducer-p signal from the front electrode 552 and a Transducer-n signal from the back electrode 554. The induced signals Transducer-pTransducer-p and Transducer-n are conveyed by wires from the electrodes 552, 554 to the wired monitor 504.

The wired monitor 504 is configured to process signals from the transducers 520, 522 and display indications of fetal heartbeat and uterine contractions. An amplifier 560 is configured and coupled to receive the deflection voltages Defl+, Defl−, amplify these signals, and provide the amplified deflection signals to a display 562. The display 562 is configured to display a visual indication of the uterine contractions, e.g., rate, magnitude, duration. The amplified deflection signals may be processed by a signal processor 564 before being conveyed to the display 562. The induced signals Transducer-p, Transducer-n corresponding to the fetal heartbeat are provided to the signal processor 564, that processes these signals and provides indications of the fetal heartbeat to the display 562 that displays visual indications of the heartbeat, e.g., intensity and direction (expanding/contracting) of fetal heart movement over time.

Patient monitoring systems have been in use for decades. Even very old systems remain operational, and the users of these systems may have used the systems for years and thus may be very comfortable and familiar with their operation.

SUMMARY

An example patient monitoring system includes: a biomedical sensor including: a transducer configured to sense a biological function and to produce an analog signal corresponding to the biological function; a sensor converter communicatively coupled to the transducer and configured to convert the analog signal to a converted signal; and a transmitter communicatively coupled to the sensor converter and configured to produce a communication, based on the converted signal, that is indicative of one or more values of the biological function, and to send the communication wirelessly; and a base station configured to communicate wirelessly with the biomedical sensor, the base station including: a receiver configured to receive the communication wirelessly and to produce a receiver output signal corresponding to the communication; a base station interface communicatively coupled to the receiver and configured to produce a base station output signal indicative of the one or more values of the biological function; and at least one output port communicatively coupled to the base station interface to receive the base station output signal, the at least one output being configured to be hard-wire connected to a display that is configured to display information indicative of the biological function.

Implementations of such a system may include one or more of the following features. The analog signal is a first analog signal and the base station interface comprises a base station converter configured to produce a second analog signal as the base station output signal. The transducer comprises a tocodynamometer transducer and the system comprises a processor configured to send a calibration signal to cause the transducer to be calibrated. The processor is configured to send the calibration signal in response to the biomedical sensor being disposed proximate to the base station. To determine that the biomedical sensor is disposed proximate to the base station, the processor is configured to determine that the base station is charging the biomedical sensor. The processor is a base station processor disposed in the base station and configured to cause the calibration signal to be sent to the biomedical sensor, the calibration signal indicating for a sensor processor disposed in the biomedical sensor to calibrate the transducer. The processor is a sensor processor disposed in the biomedical sensor and coupled to the transducer, the sensor processor being configured to send the calibration signal to the transducer to cause the transducer to adjust a variable parameter of the transducer. The processor is configured to send the calibration signal in response to the biomedical sensor being docked to the base station. The transducer includes: a Wheatstone bridge configured to be calibrated by adjustment of a variable resistor of the Wheatstone bridge; or a voice coil configured to be calibrated by adjustment of a current supplied to a coil of the voice coil.

Also or alternatively, implementations of such a system may include one or more of the following features. The biomedical sensor further includes a sensor processor and the base station further includes a base station processor, where the sensor processor and the base station processor are configured to perform a handshake to establish exclusive communication between the biomedical sensor and the base station. The sensor processor is, or the base station processor is, or the sensor processor and the base station processor are, configured to initiate the handshake in response to the biomedical sensor being disposed proximate to the base station. The sensor processor and the base station processor are configured to communicate with each other, to the exclusion of other base stations or other biomedical sensors, following the handshake until another handshake occurs between the base station processor and either the sensor processor or another sensor processor. The transducer is an ultrasound transducer, and the sensor converter includes a quadrature modulator configured to convert the analog signal such that the converted signal includes quadrature signal components. The base station output is a digital signal.

Another example patient monitoring system includes: a biomedical sensor configured to be attached to a patient and including: a sensor processor; a sensor transceiver communicatively coupled to the sensor processor; and a measurement unit including: an ultrasound unit configured to sense a fetal heartbeat and provide fetal heartbeat information; and/or a tocodynamometer configured to sense uterine contractions and provide uterine contraction information; the transceiver being communicatively coupled to the measurement unit and configured to transmit, wirelessly, biomedical monitoring signals indicative of the fetal heartbeat information and/or the uterine contraction information; and a base station including: a base station transceiver; and a base station processor communicatively coupled to the base station transceiver and configured to communicate wirelessly with the sensor processor via the base station transceiver and the sensor transceiver to establish a wireless communication arrangement between the biomedical sensor and the base station to inhibit devices other than the base station from determining the fetal heartbeat information or the uterine contraction information from the biomedical monitoring signals.

Implementations of such a system may include one or more of the following features. The base station processor is configured to initiate establishment of the wireless communication arrangement in response to the biomedical sensor coming in close proximity to the base station, or the base station processor is configured to initiate establishment of the wireless communication arrangement in response to the biomedical sensor being docked with the base station, or a combination thereof. The base station processor is configured to communicate with the sensor processor according to the wireless communication arrangement until the biomedical sensor leaves close proximity to the base station and either the biomedical sensor or another biomedical sensor comes in close proximity to the base station, or the base station processor is configured to communicate with the sensor processor according to the wireless communication arrangement until the biomedical sensor is de-docked from the base station and either the biomedical sensor or another biomedical sensor is docked with the base station, or a combination thereof. The measurement unit includes the tocodynamometer and the base station processor is configured to send a calibration signal to the biomedical sensor to cause the biomedical sensor to calibrate the tocodynamometer, the base station processor being configured to send the calibration signal in response to the biomedical sensor coming in close proximity to the base station, or the biomedical sensor being docked with the base station, or a combination thereof.

An example of a biological function sensing and reporting method includes: measuring a biological function at a sensor; providing an analog signal indicative of a value of the biological function; wirelessly transmitting an indication of the value of the biological function from the sensor to a base station; producing, at the base station, an output signal based on the indication of the value of the biological function; and providing the output signal to an output port of the base station, the output port being configured to be hard-wire connected to a monitor.

Implementations of such a method may include one or more of the following features. The analog signal is a first analog signal and producing the output signal comprises producing a second analog signal by attempting to reproduce the first analog signal. The method further includes displaying a visual indication of the value of the biological function on a display of the monitor.

DETAILED DESCRIPTION

Techniques are discussed herein for monitoring fetal heart rate and labor contractions. For example, an ultrasound unit may include an ultrasound transducer that sends ultrasound signals, receives ultrasound signals reflected from a fetal heart, and wirelessly transmit indications of a fetal heartbeat to a base station. A TOCO unit may include a TOCO configured to measure uterine contractions and wirelessly transmit indications of the uterine contractions to the base station. The base station converts the indications of the fetal heartbeat and the indications of the uterine contractions into monitor-input signals expected by a monitor of a wired patient monitoring system and provides the monitor-input signals to the monitor. The monitor-input signals may be analog signals that are attempted reproductions of analog signals produced by the ultrasound unit and/or the TOCO unit measuring fetal heart movement and uterine contractions, respectively. The monitor-input signals may be digital signals representative of the measurements from the ultrasound unit and/or the TOCO unit. The ultrasound unit and the TOCO unit may be disposed in a single housing that may be attached, e.g., strapped, to patient. Other configurations, however, may be used.

Items and/or techniques described herein may provide one or more of the following capabilities, as well as other capabilities not mentioned. Patient mobility during labor may be increased. Patient mobility during labor may be increased while allowing personnel to use familiar monitor equipment. Accuracy of equipment for measuring labor contractions may be maintained, e.g., automatically with triggered calibration. Fetal heart rate may be determined without phase or frequency locking a local oscillator of a fetal heart rate monitor with a clock of an ultrasound transmitter. A wireless fetal heart rate sensor may be backwards compatible with wired fetal heart rate monitoring equipment. Tripping hazards associated with wired biomedical sensors may be reduced or eliminated. Other capabilities may be provided and not every implementation according to the disclosure must provide any, let alone all, of the capabilities discussed. Further, it may be possible for an effect noted above to be achieved by means other than that noted, and a noted item/technique may not necessarily yield the noted effect.

Figure 1:
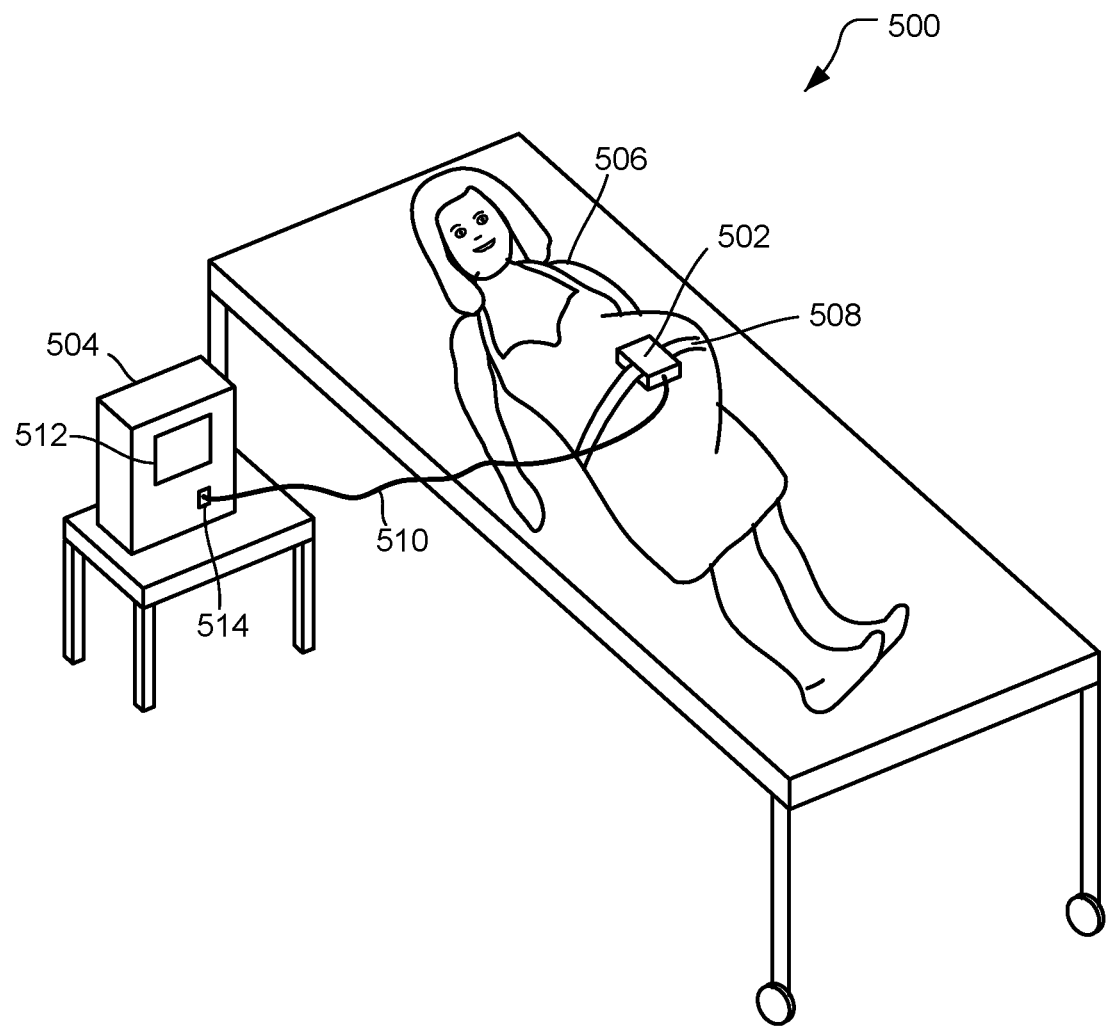
FIG. 1 is a perspective view of a wired patient monitoring system in use with a patient.
Figure 2:
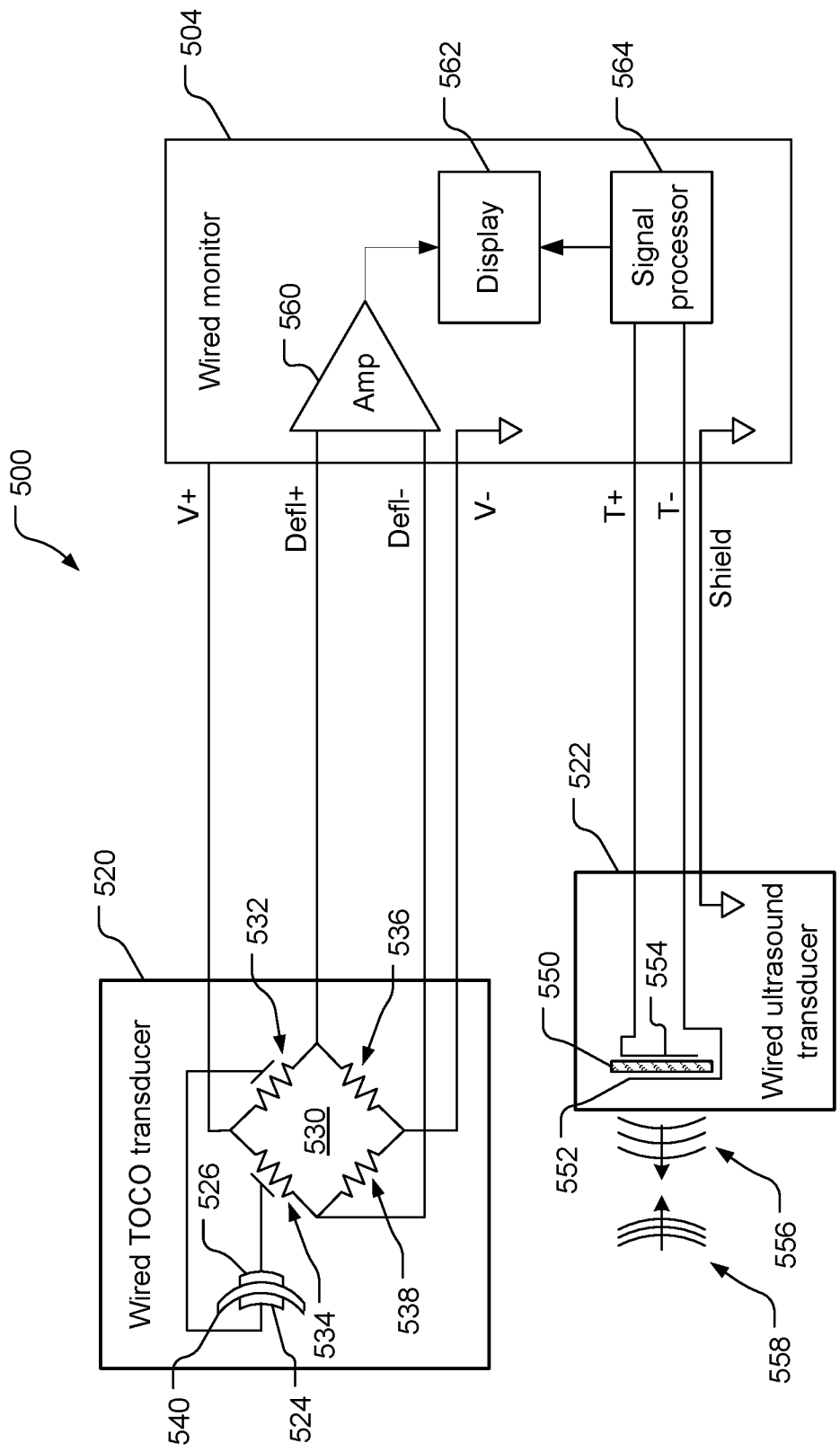
FIG. 2 is a simplified schematic of the patient monitoring system shown in FIG. 1.
Figure 3:
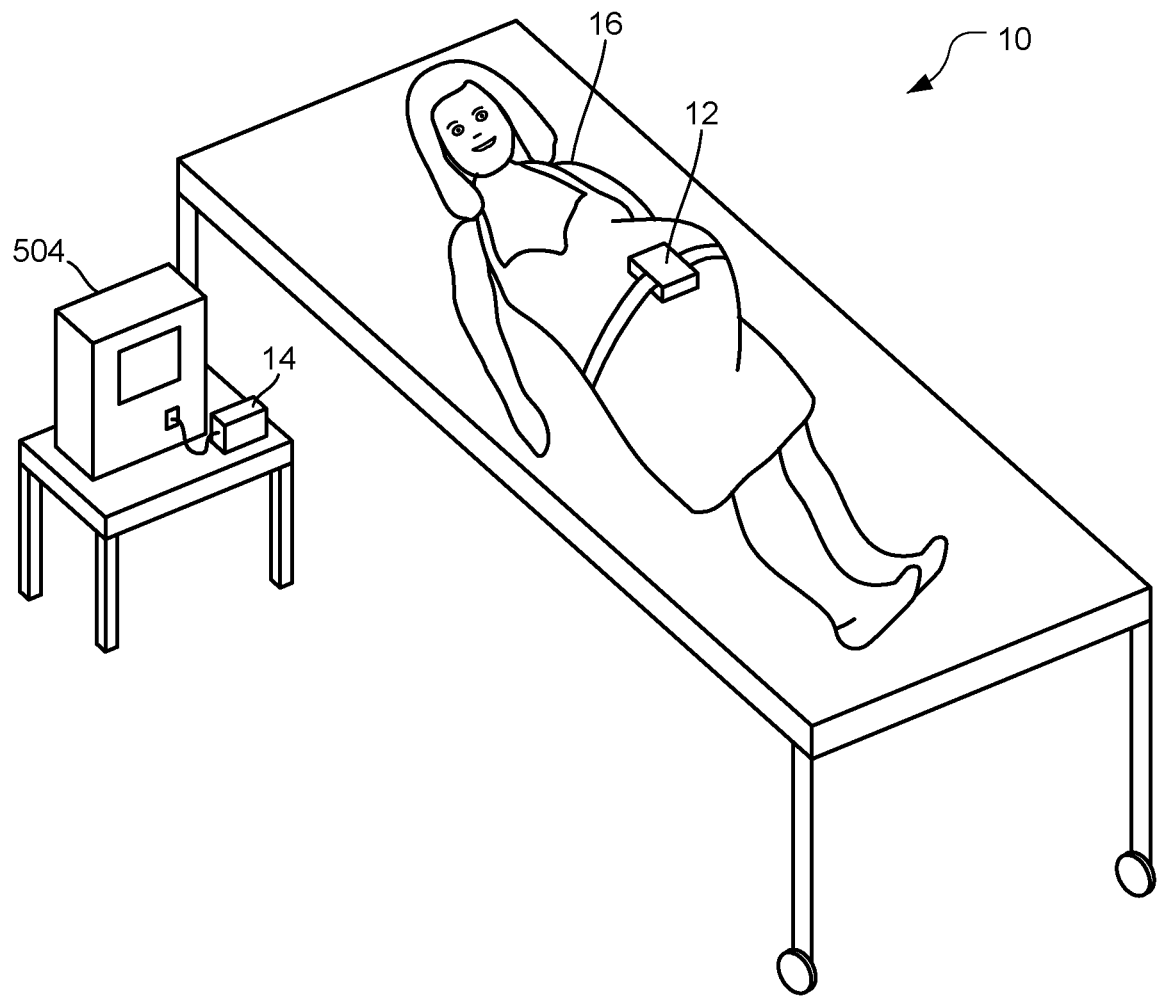
FIG. 3 is a perspective view of a wireless patient monitoring system in use with a patient.

Referring to FIG. 3, a wireless patient monitoring system 10 includes a biomedical sensor 12, a base station 14, and the monitor 504 (see FIGS. 1-2). The sensor 12 and the base station 14 are configured to monitor fetal heartbeat inside a patient 16, monitor uterine contractions of the patient 16, allow the patient to move (e.g., walk) away from the monitor 504 in a wireless, untethered fashion, while being compatible with the legacy wired monitor 504. The system 10 is wireless in that communications between the sensor 12 and the base station 14 are wireless, over-the-air communications although the base station 14 is wire-connected to the monitor 504. For example, communications between the base station 14 and the sensor 12 may be Wi-Fi communications, or communications according to another wireless communication protocol such as BLUETOOTH® wireless communication protocol.

Figure 4:
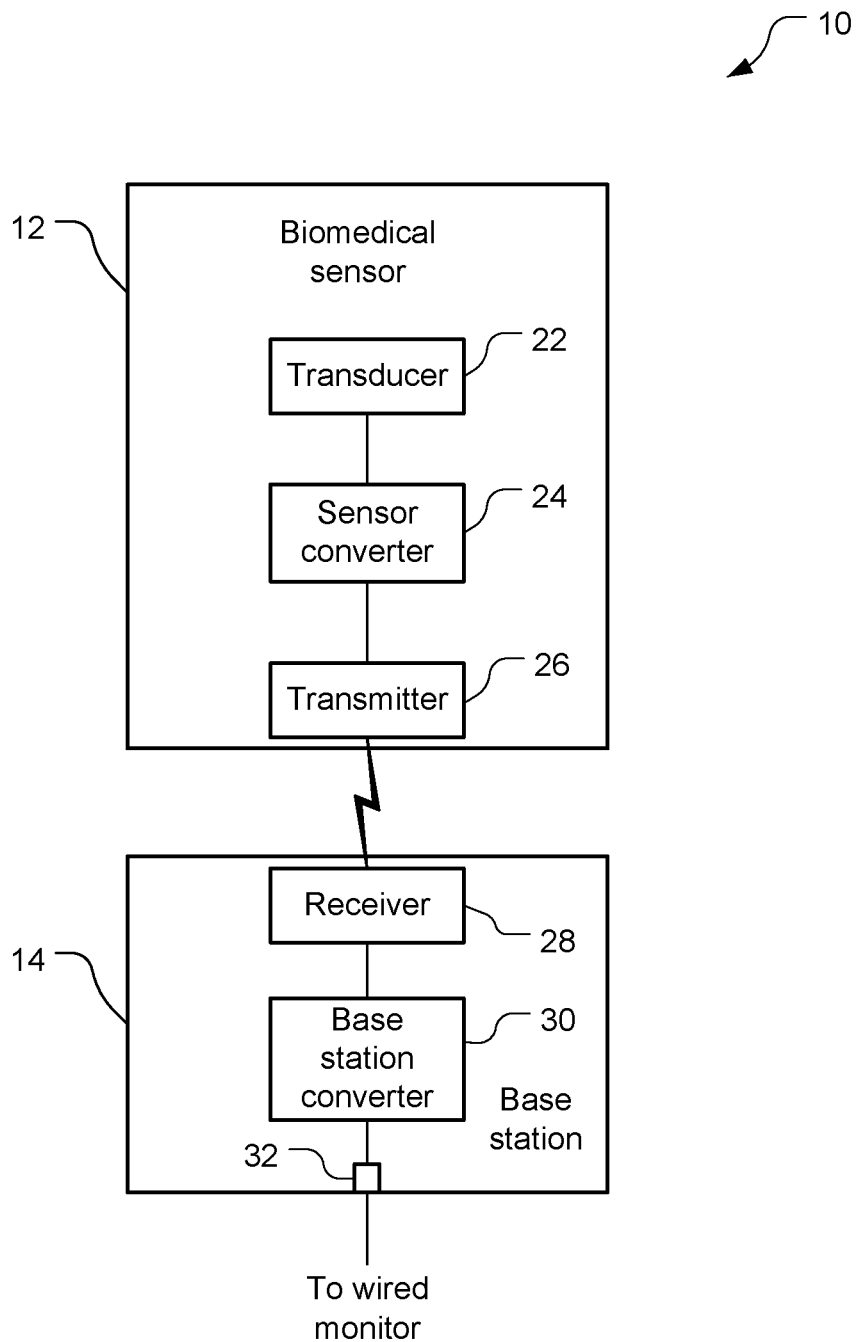
FIG. 4 is a block diagram of an example of components of a biomedical sensor and a base station of the system shown in FIG. 3.

Referring also to FIG. 4, showing an example of the system 10, an example of the biomedical sensor 12 of the patient monitoring system 10 includes a transducer 22, a sensor converter 24, and a transmitter 26 while an example of the base station of the system 10 includes a receiver 28, a base station converter 30, and an output port 32. The transducer 22 is configured to sense a biological function and to produce a first analog signal corresponding to the biological function. For example, the transducer 22 may be an ultrasound transducer or a TOCO transducer or another type of transducer. For a TOCO transducer, the transducer 22 may be a Wheatstone bridge configured to be calibrated by adjustment of a variable resistor, or a voice coil configured to be calibrated by adjustment of an amount of current provided to the voice coil. With the transducer including a TOCO transducer, the system may include a processor configured to send a calibration signal to the TOCO transducer. The processor may send the calibration signal in response to the biomedical sensor being disposed proximate to the base station 14 (e.g., within wireless charging range of the base station 14, being wirelessly charged by the base station 14, being charged by the base station 14 with a physical (e.g., hard-wired) connection, docked to the base station 14, etc.). The processor may be in the base station 14 and configured to cause the calibration signal to be sent to the biomedical sensor 12, with the calibration signal indicating for a sensor processor in the biomedical sensor 12 to calibrate the transducer 22. The processor could be disposed in the biomedical sensor 12 and configured to send the calibration signal to the transducer 22 to cause the transducer 22 to adjust a variable parameter (e.g., a variable resistance) of the transducer 22. The calibration signal may be sent from the base station 14 to the biomedical sensor 12 wirelessly and/or via a wired (physical) connection (e.g., if the biomedical sensor 12 is docked to the base station 14).

The sensor converter 24 is communicatively coupled to the transducer 22 and configured to convert the first analog signal to a converted signal. For example, the converted signal may be another analog signal, e.g., a frequency-modulated version of the analog signal from the transducer 22, or a digital signal indicative of the analog signal from the transducer 22. In the latter case, the sensor converter 24 may include, or be, an analog-to-digital converter. The sensor converter 24 may comprise a quadrature modulator configured to convert an analog signal into quadrature signal components, e.g., if the transducer 22 is an ultrasound transducer.

The transmitter is communicatively coupled to the sensor converter 24 and configured to produce a communication based on the converted signal and indicative of one or more values of the biological function, and to send the communication wirelessly, e.g., to the base station 14. The transmitter 26 includes an antenna and may be part of a transceiver that is configured to communicate bi-directionally.

The base station 14 is configured to communicate wirelessly with the biomedical sensor 12. The receiver 28 is configured to receive the communication from the transmitter 26 wirelessly and to produce a receiver output signal corresponding to the communication. The receiver 28 includes an antenna and may be part of a transceiver that is configured to communicate bi-directionally. The base station converter 30 is communicatively coupled to the receiver 28 and configured to produce a second analog signal indicative of the one or more values of the biological function. The output port 32 is communicatively coupled to the base station converter 30 to receive the second analog signal, and is configured to be hard-wire connected to a display that is configured to display information indicative of the biological function. For example, the output port 32 can be hard-wire connected to an input port of the monitor 504, with the input port being communicatively coupled to a display of the monitor 504. The biomedical sensor 12 may include a sensor processor, and the base station 14 may include a base station processor configured to perform a handshake with the sensor processor to establish exclusive communication between the biomedical sensor and the base station. For example, following the handshake, the sensor processor and the base station processor may communicate with each other to the exclusion of other base stations or other biomedical sensors until another handshake occurs between the base station processor and either the same sensor processor or another sensor processor.

Figure 5:
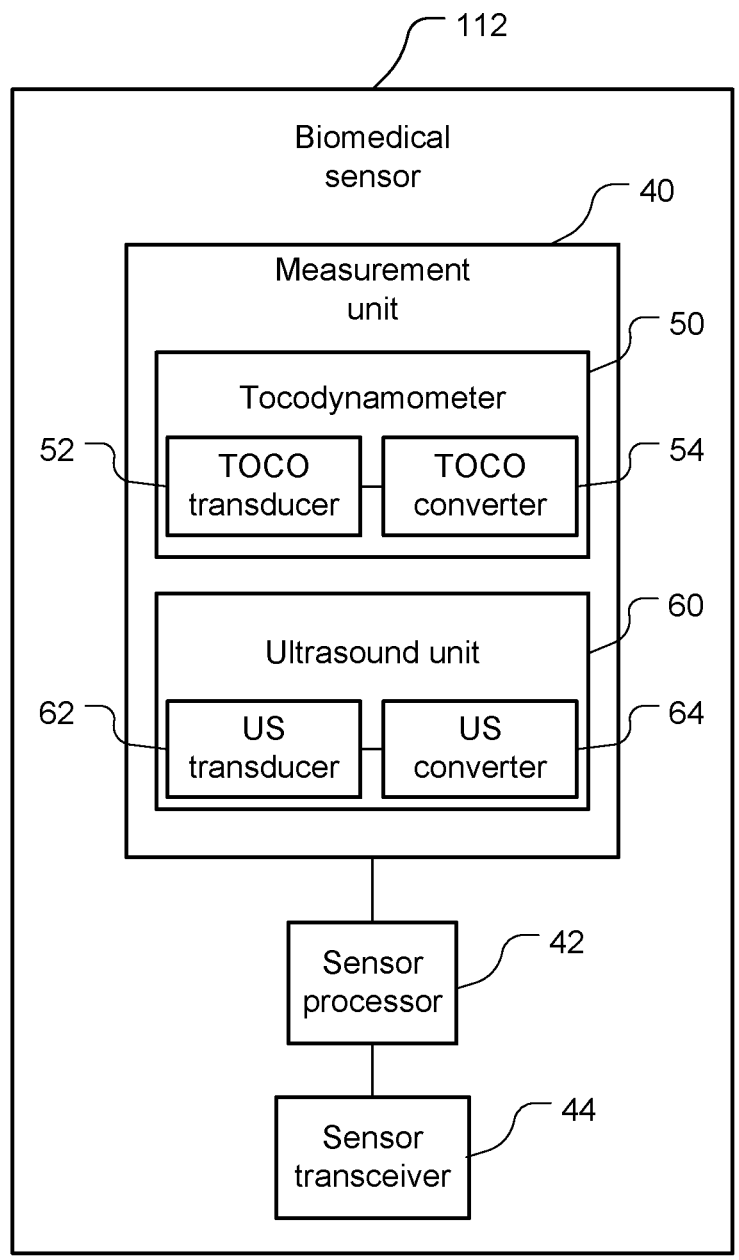
FIG. 5 is a block diagram of an example of components of the biomedical sensor shown in FIG. 4.

Referring to FIG. 5, with further reference to FIGS. 3-4, a biomedical sensor 112, which is another example of the biomedical sensor 12 shown in FIGS. 3-4, includes a measurement unit 40, a sensor processor 42, and a sensor transceiver 44. The measurement unit 40 is configured to obtain measurement of biological functions. The sensor processor 42 is configured to communicate wirelessly with the base station 14 via the sensor transceiver 44 to provide information regarding the biological functions to the base station 14.

In the example of FIG. 5, the measurement unit 40 is configured to obtain measurements of uterine contractions and a fetal heartbeat and includes a TOCO 50, including a TOCO transducer 52 and a TOCO converter 54, and an ultrasound (US) unit 60, including a US transducer 62 and a US converter 64. The TOCO transducer 52 is configured to sense uterine contractions and provide uterine contraction information to the TOCO converter 54. The TOCO transducer 52 is configured to transduce indications of uterine contractions into information, e.g., analog signals, indicative of the uterine contractions. The TOCO transducer 52 is communicatively coupled to the TOCO converter 54 and configured to provide the information, e.g., the analog signals, indicative of the contractions to the TOCO converter 54. The TOCO converter 54 is configured to convert the analog signals from the TOCO transducer 52 into digital information indicative of the uterine contractions. The US transducer 62 is configured to sense a fetal heartbeat and provide fetal heartbeat information to the US converter 64. The US transducer 62 is configured to transduce wireless US signals, e.g., that have been Doppler shifted by a fetal heart, into information, e.g., analog signals, indicative of the fetal heartbeat. The US transducer 62 is communicatively coupled to the US converter 64 and configured to provide the information, e.g., the analog signals, indicative of the fetal heartbeat to the US converter 64. The US converter 64 is configured to convert the analog signals from the US transducer 62 into digital information indicative of the fetal heartbeat. The sensor transducer 22 shown in FIG. 3 may include the TOCO transducer 52 and the US transducer 62.

The sensor converter 24 shown in FIG. 3 may include the TOCO converter 54 and the US converter 64.

The sensor transceiver 44 is communicatively coupled to the measurement unit 14, here via the sensor processor 42, and configured to transmit, wirelessly, biomedical monitoring signals indicative of the information regarding the sensed biological functions. Here, the sensor transceiver 44 will wirelessly transmit biomedical monitoring signals indicative of the fetal heartbeat information and the uterine contraction information. The wirelessly transmitted signals may convey digital information such as TCP/IP (transmission control protocol/internet protocol) packets of information. The sensor transceiver 44 includes the transmitter 26 shown in FIG. 3, and includes one or more appropriate antennas for transducing electric signals into wireless electromagnetic signals and sending the EM signals, and for receiving information wirelessly, e.g., EM signals, and for transducing the received wireless signals into electric signals. Alternatively, the sensor transceiver 44 may be a sensor transmitter only, and not configured to receive wireless signals, transduce those signals, and provide the transduced signals to the sensor processor 42.

Figure 6:
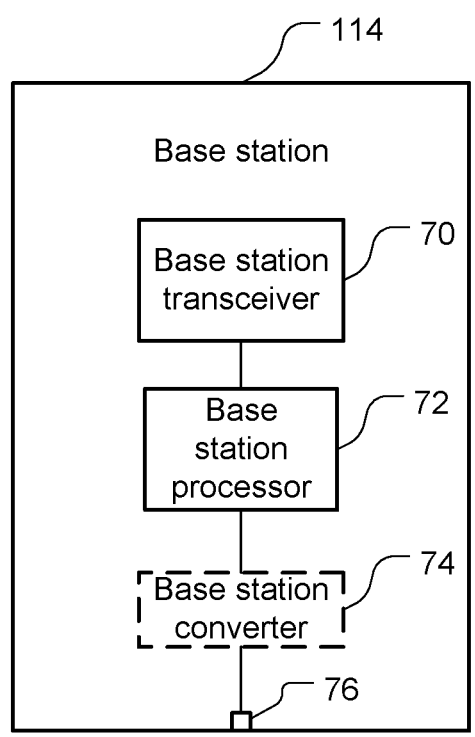
FIG. 6 is a block diagram of an example of components of the base station shown in FIG. 4.

Referring to FIG. 6, with further reference to FIGS. 1-5, a base station 114, which is another example of the base station 14, includes a base station transceiver 70, a base station processor 72, optionally a base station converter 74, and an output port 76. The base station transceiver 70 includes the receiver 28 shown in FIG. 4, and includes one or more appropriate antennas for transducing electric signals into wireless electromagnetic signals and sending the EM signals, and for receiving information wirelessly, e.g., EM signals, and for transducing the received wireless signals into electric signals. Alternatively, the base station transceiver 70 may be a base station receiver only, and not configured to transmit wireless signals.

The base station processor 72 is communicatively coupled to the base station transceiver and configured to communicate wirelessly with the sensor processor 42 via the base station transceiver 70 and the sensor transceiver 44 to establish a wireless communication arrangement between the biomedical sensor 112 and the base station 114. For example, the base station processor 72 may be configured to initiate establishment of the wireless communication arrangement in response to the biomedical sensor 112 coming in close proximity to the base station 114 and/or in response to the biomedical sensor 112 being docked with the base station 114. The base station processor 72 may be configured to communicate with the sensor processor 42 according to the wireless communication arrangement until the biomedical sensor 112 leaves close proximity to the base station 114 and either the biomedical sensor 112 or another biomedical sensor comes in close proximity to the base station 114, and/or until the biomedical sensor 112 is de-docked from the base station 114 and either the biomedical sensor 112 or another biomedical sensor is docked with the base station 114.

The base station processor 72 may be configured to establish the wireless communication arrangement to inhibit devices other than the base station 114 from determining the fetal heartbeat information or the uterine contraction information from the biomedical monitoring signals from the biomedical sensor 112. That is, only (exclusively) the base station 114, and no other base station and possibly no other device, will (in all likelihood) be able to interpret the biomedical monitoring signals in order to determine the fetal heartbeat information or the uterine contraction information. For example, the base station 114 and the biomedical sensor 112 may agree upon a cryptographic protocol and/or one or more cryptographic keys such that the biomedical sensor 112, e.g., the sensor processor 42, may encrypt biomedical information (e.g., the fetal heartbeat information and the uterine contraction information) and send the encrypted biomedical information to the base station 114. Thus, it will be highly unlikely, although not theoretically impossible, for any other device to interpret the biomedical information. Therefore, for purposes of this discussion, only the base station 114, that has the appropriate cryptographic key for deciphering the encrypted biomedical information will be able to decrypt the biomedical information. The base station processor 72 is communicatively coupled to the base station converter 74, if present, and is configured to provide the (decrypted) biomedical information to the base station converter 74. The base station 114 may, however, interpret biomedical information from other biomedical sensors, e.g., if a protocol and/or encryption keys have been established between the base station 114 and another biomedical sensor. Further, other communications may not be encrypted for transfer between, or otherwise exclusive between, the biomedical sensor 112 and the base station 114.

The base station processor 72 may be configured to send a calibration signal to the biomedical sensor 112. For example, the base station processor 72 may be configured to send, in response to the biomedical sensor 112 coming in close proximity to the base station 114 and/or being docked to the base station 114, the calibration signal to the biomedical sensor 112 to calibrate the TOCO 50.

The base station converter 74 is configured to convert the biomedical information into a format that can be used by the monitor 504. For example, the converter 74 may be configured to convert the biomedical information from digital form into analog form, including the Defl+, Defl−, Transducer-n, and Transducer-p analog signals that the legacy monitor 504 is configured to receive and process to display corresponding indications for a user. The processor 72 (if the converter 74 is not present), or the converter 74 (if present), is configured to provide the respective output signals to the output port 76 that is configured to be hard-wire connected to the monitor 504. For example, the output port 76 may be a connector configured to receive a shielded cable configured to be connected to the monitor 504, e.g., with an appropriate connector at another end of the cable.

Figure 7:
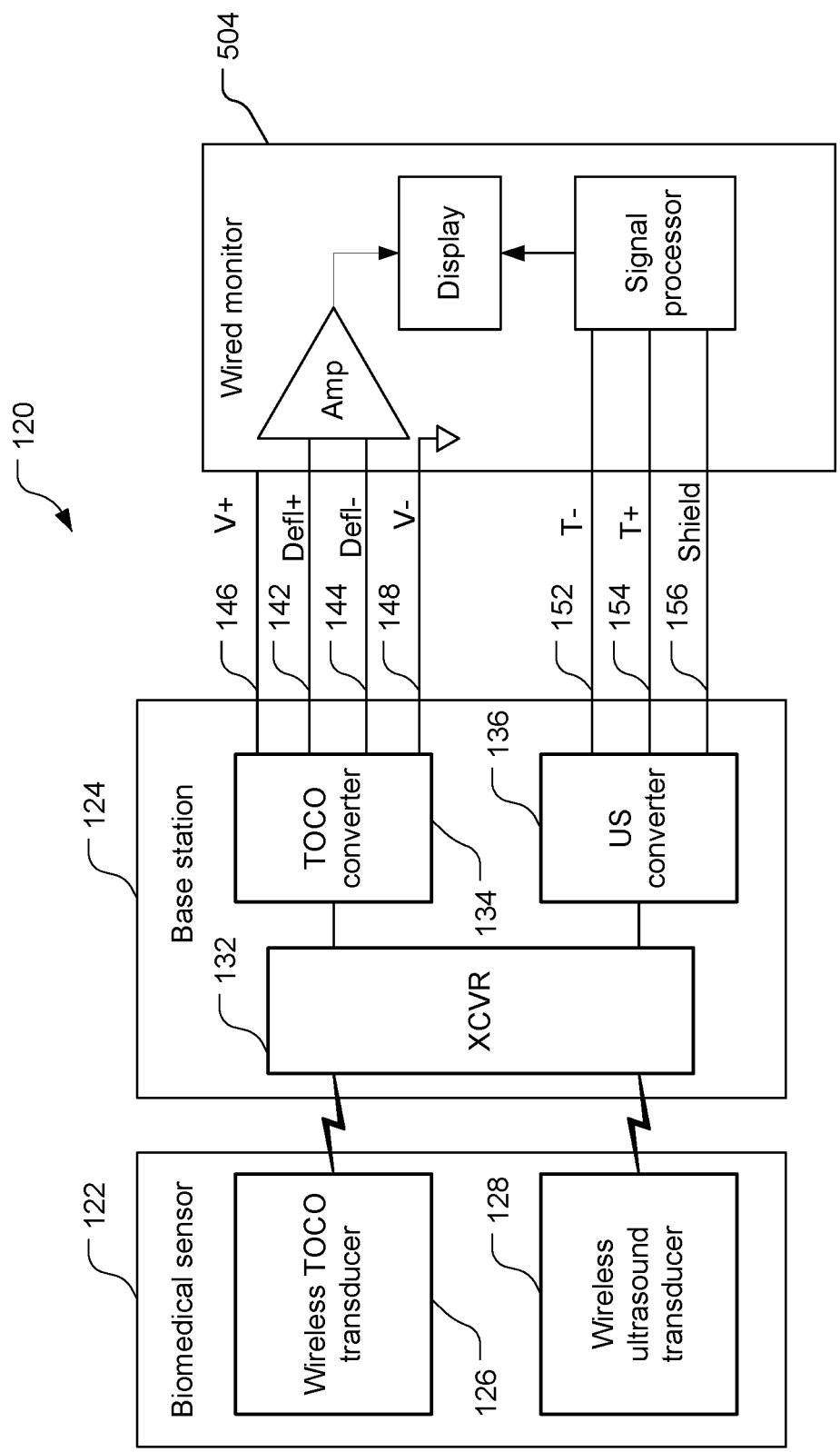
FIG. 7 is a block diagram of an example of components of the system shown in FIG. 3 showing wireless and wired connections and signals conveyed by wires to a wired monitor.

Referring to FIG. 7, with further reference to FIGS. 3-6, a wireless patient monitoring system 120, which is another example of the wireless patient monitoring system 10, includes a biomedical sensor 122, a base station 124, and the monitor 504. Here, the biomedical sensor 122 includes a wireless TOCO transducer 126 and a wireless ultrasound transducer 128. Although the wireless TOCO transducer 126 and the wireless ultrasound transducer 128 are shown in the biomedical sensor 122, the wireless TOCO transducer 126 and the wireless ultrasound transducer 128 may be physically separate items and may or may not be included in a single housing. The transducers 126, 128 may be similar to the transducers 52, 62 discussed with respect to FIG. 5 (and may include the converters 54, 64, the processor 42, and the transceiver 44 discussed with respect to FIG. 5, or one or more apparatus similar to one or more of these apparatus). The base station 124 includes a transceiver 132, a TOCO converter 134, and a US converter 136. The TOCO converter 134 is configured to convert digital information, e.g., one or more packets of data, received via the transceiver 132 from the TOCO transducer 126, regarding uterine contractions into analog signals Defl+ and Defl− and to provide these signals to the monitor 504 via hard-wire lines 142, 144.

The Defl+ and Defl− signals may be reproductions (although possibly not identical reproductions) of Defl+ and Defl− signals produced by the wireless TOCO transducer 126, e.g., a strain gauge in the transducer 126, to emulate the signals that would be received by the monitor 504 if a wired TOCO transducer was used. The base station 124 also provides reference voltages V+, V− to the monitor 504 via hard-wire lines 146, 148. The US converter 136 is configured to convert digital information, e.g., one or more packets of data, received via the transceiver 132 from the US transducer 128, regarding fetal heartbeat into analog signals Transducer-negative (S-T-n in FIG. 7) and Transducer-positive (S-T-p in FIG. 7) and to provide these signals to the monitor 504, here via a shielded cable including hard-wire lines 152, 154, and a shield 156.

Figure 8:
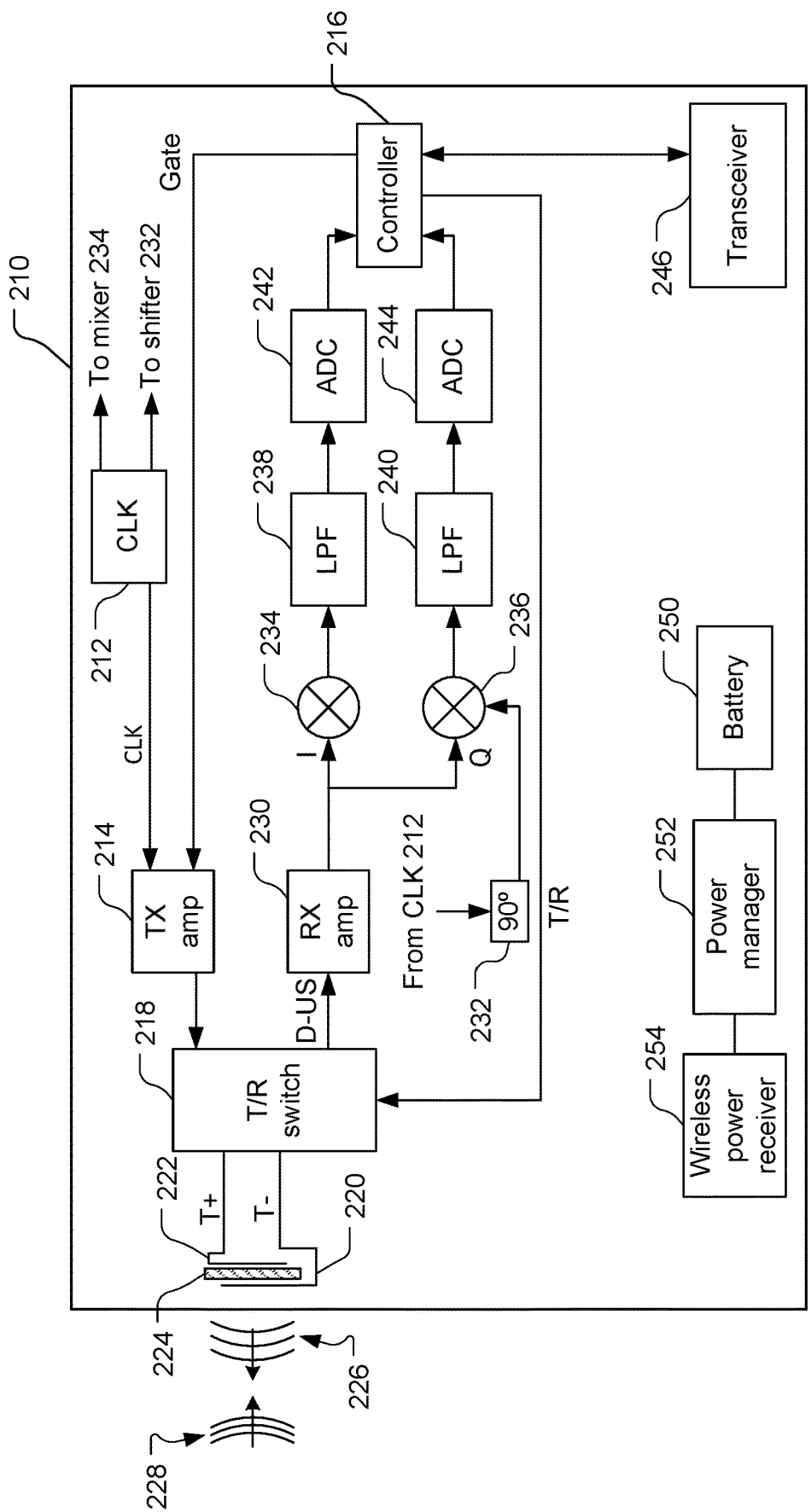
FIG. 8 is a simplified schematic of components of an example of a wireless ultrasound transducer shown in FIG. 7.

Referring to FIG. 8, with further reference to FIGS. 3-7, an example of a CTG system 210, which may be an example of the biomedical sensor 12 shown in FIG. 4, an example of the US unit 60 shown in FIG. 5, or an example of the wireless US transducer 128 shown in FIG. 7, includes the components shown. The components shown in FIG. 8 are coupled to each other as shown by lines between the components, with arrows on respective lines indicating directions of signal flow. The CTG system 210 is configured to detect fetal heart movement using ultrasound signals, to wirelessly convey indications of this movement, and to be charged wirelessly.

The CTG system 210 includes a clock (CLK) 212 that is configured to provide an ultrasound signal. For example, the clock 212 may provide a drive signal CLK and the clock 212 is coupled to a transmission amplifier (TX amp) 214 to provide the drive signal to the transmission amplifier 214. A frequency of the drive signal may be selected to provide significant samples, e.g., for averaging and good signal-to-noise ratio, while having low attenuation in tissue. The transmission amplifier 214 is configured to amplify the drive signal to produce an amplified drive signal, and to output the amplified drive signal in accordance with a gate signal (Gate) received from a controller 216. The controller 216 is configured to provide the gate signal such that the transmission amplifier 214 outputs the amplified drive signal only when the gate signal indicates to help put, e.g., when the gate signal is high. The transmission amplifier 214 may only amplify the clock signal from the clock 212 only when the clock signal indicates to help put the amplified drive signal. For example, the controller 216 may provide the gate signal to control the transmission amplifier 214 to output the amplified drive signal in pulses. The transmission amplifier 214 is coupled to a transmit/receive (T/R) switch 218 to provide the amplified drive signal to the T/R switch 218.

The T/R switch 218 is coupled and configured to provide excitation signals, based on the received amplified drive signal, to a piezoelectric element to produce ultrasound signals. The T/R switch 218 may be configured to use the amplified drive signal to produce and provide an outbound Transducer-positive signal (T+) to a front electrode 222 and to produce and provide an outbound Transducer-negative signal (T−) to a back electrode 220 to drive the electrodes 220, 222 to excite a piezoelectric element 224 to produce and transmit outbound ultrasound signals 226. With the amplified drive signal provided by the transmission amplifier 214 to the T/R switch 218 being a pulsed signal, and the on/off nature of the T/R switch 218 per the T/R signal from the controller to 16, the outbound US signals 226 produced by the piezoelectric element 224 are pulsed US signals. The pulse rate of the outbound US signals 226 may be fixed at a multiple of a highest expected Doppler offset frequency.

The outbound US signals 226 may be focused on a fetal heart such that fetal heart movement will induce a Doppler shift on the outbound US signals 226 and reflect the outbound US signals 228 to produce inbound US signals 228 that are phase shifted relative to the outbound US signals 226. Movement of a target, e.g., a fetal heart, either toward or away from the piezoelectric element 224 reflecting the outbound US signals 226 will advance or retard phase of the reflected signals relative to the outbound US signals 226. In the example shown in FIG. 8, the inbound US signals 228 are compressed in time (phase advanced) relative to the outbound US signals 226 due to movement of the fetal heart toward the piezoelectric element 224 (the heart expanding after a contraction). The piezoelectric element 224 is configured to respond to receiving the inbound US signals 228 to induce inbound electric transducer signals T-p and T− in the electrodes 220, 222 that are conveyed to the T/R switch 218.

The T/R switch 218 is configured to either provide the outbound transducer signals T+, T− to the electrodes 220, 222 based on the amplified drive signal, or to provide the inbound transducer signals T+, T− from the electrodes 220, 222 to a receive amplifier (RX amp) 230 based on a value of a transmit/receive signal (T/R) received from the controller 216. The controller 216 is configured to control a value of the T/R signal (i.e., to transmit or to receive) to the T/R switch 218 based on timing of the outbound US signals 226, timing of the gate signal causing the transmission amplifier 214 to provide the amplified drive signals to the T/R switch 218, and expected timing of receipt of the inbound US signals 228 based on timing of transmission of the outbound US signals 226. The T/R switch 218 is configured to convert the inbound transducer signals T+, T− into a single inbound signal, for example, an inbound Doppler-shifted ultrasound signal D-US. The receive amplifier 230 is configured to amplify the signal D-US to about a magnitude of the amplified drive signal output by the transmit amplifier 214. The received amplifier 230 may be a self-regulating amplifier that adjusts the amplification provided by the receive amplifier 230 based on the power level of the signal D-US. The amplification provided by the receive amplifier 230 helps to compensate for attenuation due to distance from the piezoelectric element 224 and the target, e.g., the fetal heart, and for losses due to material between the piezoelectric element 224 and the target.

The amplified signal from the receiver amplifier 230 is divided and respective portions provided to an I/Q demodulator comprising a phase shifter 232 and a mixer 234. One portion of the amplified signal is provided as an I signal to the mixer to 234. Another portion of the amplified signal from the receive amplifier 230 is phase shifted by 90 degrees by the phase shifter 232 and the output from the phase shifter 232 provided as a Q signal to a mixer 236. The CTG system 210 is battery operated, as discussed more fully below, and thus the transmit power of the outbound US signals 226 may be lower than if the CTG system 210 was driven by mains power. To have approximately a similar dynamic range as if the CTG system 210 was driven by mains power to be able to receive and process the reflected inbound US signals 228, the receive amplifier 230 provides more amplification than if the CTG system 210 was driven by mains power while the I/Q demodulator provides a low noise figure. The I/Q demodulator provides good signal-to-noise ratio (SNR) while retaining the information from the signal CTG. In addition to receiving the I and Q signals, respectively, the mixers 234, 236 also respectively receive the continuous-wave drive signal CLK, or the CLK signal phase shifted by 90°, as an input. By using the same drive signal CLK for both the transmit signal and the receive local oscillator, the CTG system 210 is kept coherent. The mixers 234, 236 downconvert the 1.151 MHz signal to baseband to reveal a signal at 2 KHz of the fetal heartbeat.

The baseband signals provided by the mixers 234, 236 are provided to low pass filters (LPFs) 238, 240 and to analog-to-digital converters (ADCs) 242, 244, respectively. The LPFs 238, 240 filter aliased sideband signals and the ADCs 242, 244 digitize the respected filtered signals. The I and Q signals may be sampled by the ADCs 242, 244 has a sampling frequency such as 4 KHz. The ADCs 242, 244 provide the digitized, filtered signals to the controller 216 for further processing.

The controller 216 processes the digitized signals from the ADCs 242, 244 and provides processed information to a transceiver 246 for wireless transmission to the base station 14. For example, the controller 216 may be a microcontroller (e.g., a central processing unit (CPU)) including a non-transitory, processor-readable medium (memory) that stores instructions that are executable (directly or after compiling) for causing the controller 216 to performing corresponding functions, e.g., as discussed herein. The controller 216 may be configured to filter the digitized I and Q Signals, e.g., using a Wiener filter or a Golay filter with a running window) to clean (e.g., smooth) the I and Q signals. The controller 216 may further be configured to implement a phase-detection algorithm to extract the phase shift of the Doppler-shifted ultrasound signal D-US relative to the drive signal CLK, which corresponds to the Doppler frequency. The controller 216 may collect multiple samples of the determined Doppler frequency before conveying the Doppler frequency information to the transceiver 246. For example, the controller 216 may collect approximately 100 samples of the Doppler frequency and report the 100 samples of the Doppler frequency to the transceiver 246. The controller 216 may gather the multiple samples and form a packet, e.g., a TCP/IP packet, containing indications of the Doppler frequencies (i.e., the phase shifts). The controller 216 may perform additional processing on the samples such as averaging of samples. The transceiver 246 is configured to receive the packets of information from the controller 216 and to wirelessly transmit the packets to the base station 14, e.g., using a wireless protocol. Examples of a protocol that may be used by the transceiver 246 include a wireless local area network (WLAN) protocol such as an 802.11, a Wi-Fi protocol, the Wireless Medical Telemetry Service (WMTS) standard, the IEEE 802.15.4 Zigbee® protocol, or the Bluetooth® protocol. As discussed, the packets sent to, and by, the transceiver, have payload information indicative of the phase shift (Doppler frequency) of the inbound US signals 228. Other techniques, however, may be used such as the packets conveying information from which the phase shift may be determined, e.g., values of the I and Q signals over time.

The CTG system 210 further includes a battery 250, a power manager 252, and a wireless power receiver 254. The battery 250 is a rechargeable battery capable of being charged by power received wirelessly by the wireless power receiver 254, and of supplying energy to components of the CTG system 210, either directly or via the power manager 252. The power manager 252 is configured to regulate power received via the wireless power receiver 254 to provide power to the battery 250 and/or to other components of the CTG system 210. The wireless power receiver 254 is configured to receive power wirelessly, e.g., from the base station 14. The wireless power receiver 254 may be, for example, a coil configured to couple to a magnetic field provided by the base station 14, a plate configured to capacitively couple to the base station 14, etc.

Figure 9:
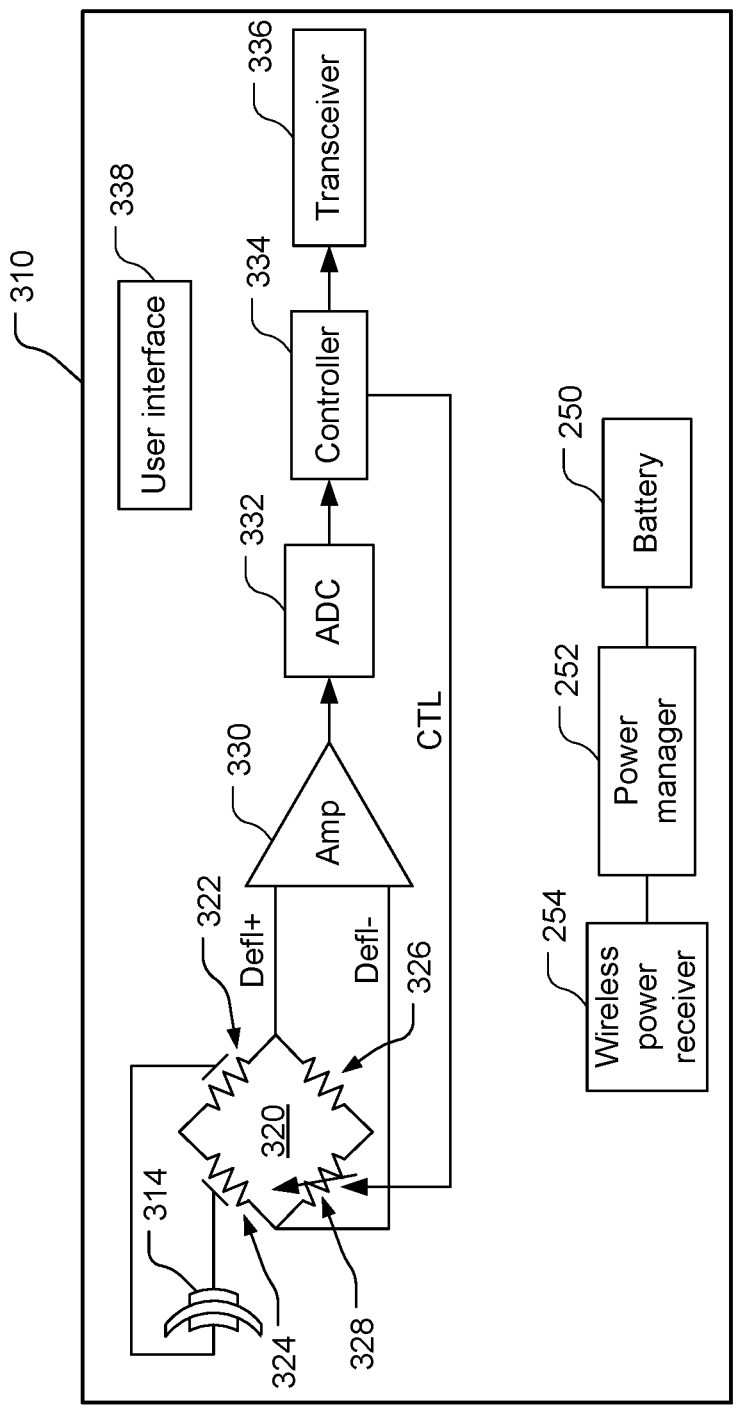
FIG. 9 is a simplified schematic of components of an example of a wireless TOCO transducer shown in FIG. 7.

Referring to FIG. 9, with further reference to FIGS. 3-7, an example of a TOCO 310, which may be an example of the biomedical sensor 12 shown in FIG. 4, an example of the tocodynamometer 50 shown in FIG. 5, or an example of the wireless TOCO transducer 126 shown in FIG. 7, includes the components shown. The components shown in FIG. 9 are coupled to each other as shown by lines between the components, with arrows on respective lines indicating directions of signal flow. The TOCO 310 in this example is configured to uterine contractions using strain gauges, to wirelessly convey indications of the contractions, and to be charged wirelessly, and may be configured to recalibrate the strain gauge.

The TOCO 310 includes two strain gauges 312, 314 that provide resistances 322, 324 of a Wheatstone bridge 320, with the bridge further including a fixed resistor 326 (i.e., has a fixed resistance), and a variable resistor 328. The variable resistor 328 (e.g., a potentiometer) is under digital control from a controller 334. Thus, a resistance of the variable resistor 328 may be set (e.g., changed) in accordance with a control signal CTL from the controller 334. The strain gauges 312, 314 are disposed on respective sides of a flexible sheet 316, e.g., a piece of metal, and are configured to measure deflection of respective sides of the flexible sheet 316 and provide resistance values for the resistors 322, 324 corresponding to the deflection. Reference voltages V+ and V− are applied to top and bottom nodes of the bridge 320 and side nodes of the bridge 320 provide Defl+ and Defl− voltages indicative of the deflection of the flexible sheet 316, and thus indicative of a uterine contraction. A magnitude difference of the deflection voltages Defl+ and Defl− is indicative of a magnitude of the contraction, and a time period over which the deflection voltages Defl+ and Defl− have a non-zero difference corresponds to a duration of the contraction. The deflection voltages Defl+ and Defl− are provided on respective wires to an amplifier 330.

The TOCO 310 further includes an amplifier 330, and ADC 332, the controller 334, and a transceiver 336 that in combination are configured to digitize and transmit indications of the Defl+ and Defl− signals. During operation, as the resistances 322, 324 provided by the strain gauges 312, 314 vary, voltages of the Defl+ and Defl− signals will vary accordingly. These signals are provided to the amplifier 330 and the amplifier 330 is configured to produce a difference signal indicative of a difference between the voltages of the Defl+ and Defl− signals. The amplifier 330 is configured and coupled to provide the difference signal to the ADC 332. The ADC 332 is configured to digitize the difference signal from the amplifier 330 and provide the digitized different signal to the controller 334. The controller 334 may collect multiple instances of the difference indicated by the difference signal to form the payload of a packet that the controller 334 provides to the transceiver 336 for wireless transmission to the base station 14. Alternatively, the controller 334 may be configured to produce and send the packet to the transceiver 336 for each instance of the determined and digitized difference indicated by the difference signal. For example, the ADC 332 may sample the difference signal at a sampling rate of 10 Hz and the controller 334 may provide a packet for each sampled difference to the transceiver 336. The transceiver 336 may be configured to transmit the packets indicative of the different signal using an appropriate wireless protocol, e.g., such as those discussed above with respect to the transceiver 246 shown in FIG. 8. The transceivers 246, 336 may be a single transceiver or part of a single transceiver, and/or the controllers 216, 334 may be a single controller or part of a single controller. The controller 334 is further configured to provide feedback for the variable resistor 328, e.g., for calibration of the bridge 320.

The controller 334 is configured to control calibration of the TOCO 310. For example, the controller 334 may respond to a signal received from the base station 14, e.g., via the transceiver 336 and/or via the wireless power receiver 254, to initiate calibration of the TOCO 310. Calibration of the TOCO 310 may be automatically initiated, e.g., upon docking of the TOCO 310 with the base station 14, upon the TOCO 310 coming in close proximity (e.g., within communication and/or charging range) to the base station 14, in response to the base station communicating with the TOCO 310, and/or in response to the base station 14 charging the TOCO 310, and/or in response to one or more other conditions being met. For example, the power manager 252 could instruct the controller 334 to perform calibration in response to the power manager 252 determining that the TOCO 310 is docked to the base station 14. The power manager 252 may be configured to determine that the TOCO 310 is docked to the base station 14, for example, by determining that the wireless power receiver 254 receives a threshold amount of charging power from the base station 14, and/or by determining that a mechanical indicator has been triggered indicating that the TOCO 310 is docked to the base station 14. Also or alternatively, the base station 14 may communicate (vias wires or via short-range wireless communication) such that the controller 334 can be triggered to initiate calibration. To perform the calibration, the controller 334 may be configured to determine a deflection value (and/or to set the variable resistor to result in a zero or near-zero deflection value) under a no-load condition, and to determine the deflection value under a known-load condition. The TOCO 310 and the base station 14 may be configured to help ensure that the TOCO will have no load with the TOCO 310 docked to the base station, e.g., with the strain gauges 312, 314 protected from being pressured. With no load on the flexible sheet 316, the controller 334 may adjust the resistance of the variable resistor 328 by adjusting the control signal CTL until a deflection value in accordance with the deflection signals Defl+, Defl− is within a threshold of zero for a threshold amount of time. Alternatively, the controller 334 could store an indication of the deflection value under the no-load condition. The controller 334 may indicate to an operator, e.g., through a user interface 338, to attach a load to the flexible sheet. The controller 334 may indicate to the user to attach a known load magnitude, e.g., of a known weight that is sufficiently heavy such that measurement values with no load and the known load will enable a desirable measurement resolution for the TOCO 310, and/or the operator may indicate to the controller 334 through the user interface the magnitude (e.g., weight) of the load. The controller 334 may determine and store a loaded deflection value under the load condition. The controller 334 may determine a relationship of deflection-to-load (corresponding to deflection-to-intensity of a uterine contraction) using the no-load deflection value (which may be zero) and the loaded deflection value. For example, the controller 334 may assume a linear relationship and determine a slope of a line using the no-load deflection value, the load deflection value, and the magnitude of the load (e.g., weight). The controller 334 may use this relationship (e.g., slope) to determine a load magnitude (corresponding to a contraction intensity) based on a measured deflection value with the TOCO 310 in use, with the flexible sheet 316 applied to an abdomen of the patient 506.

The TOCO 310 further includes the battery 250, the power manager 252, and the wireless power receiver 254 of the CTG system 210 shown in FIG. 8. The power manager 252 is configured to use energy received via the wireless power receiver 254 and/or energy stored by the battery 252 power the components of the TOCO 310. Further, the power manager 252 may be configured to provide an instruction conveyed by the magnetic field coupled to by the wireless power receiver 254 to the controller 334, e.g. to initiate calibration of the bridge 320. For example, the power manager 252 may be comprised, at least partially, by the controller 216 or be communicatively coupled to the controller 216 to supply communication signals received via the wireless power receiver 254 to the controller 216. For example, a magnetic field to which the wireless power receiver 254 couples may be altered to convey information, e.g. an instruction to calibrate the bridge, and this information may be provided to the controller 334. The transceiver 336 may be a transmitter only, especially if the power manager 252 receives instruction signals for calibration via the wireless power receiver 254, or if the power manager 252 otherwise instructs the controller 334 to perform the calibration. The power manager 252 may be configured to communicate with the base station 14, e.g., via the wireless power receiver 254 and/or the transceiver 336, to inform the base station 14 that the wireless power receiver 254 is receiving power from the base station 14 and thus that the base station 14 may safely send a charging level of power to the TOCO 310.

Figure 10:
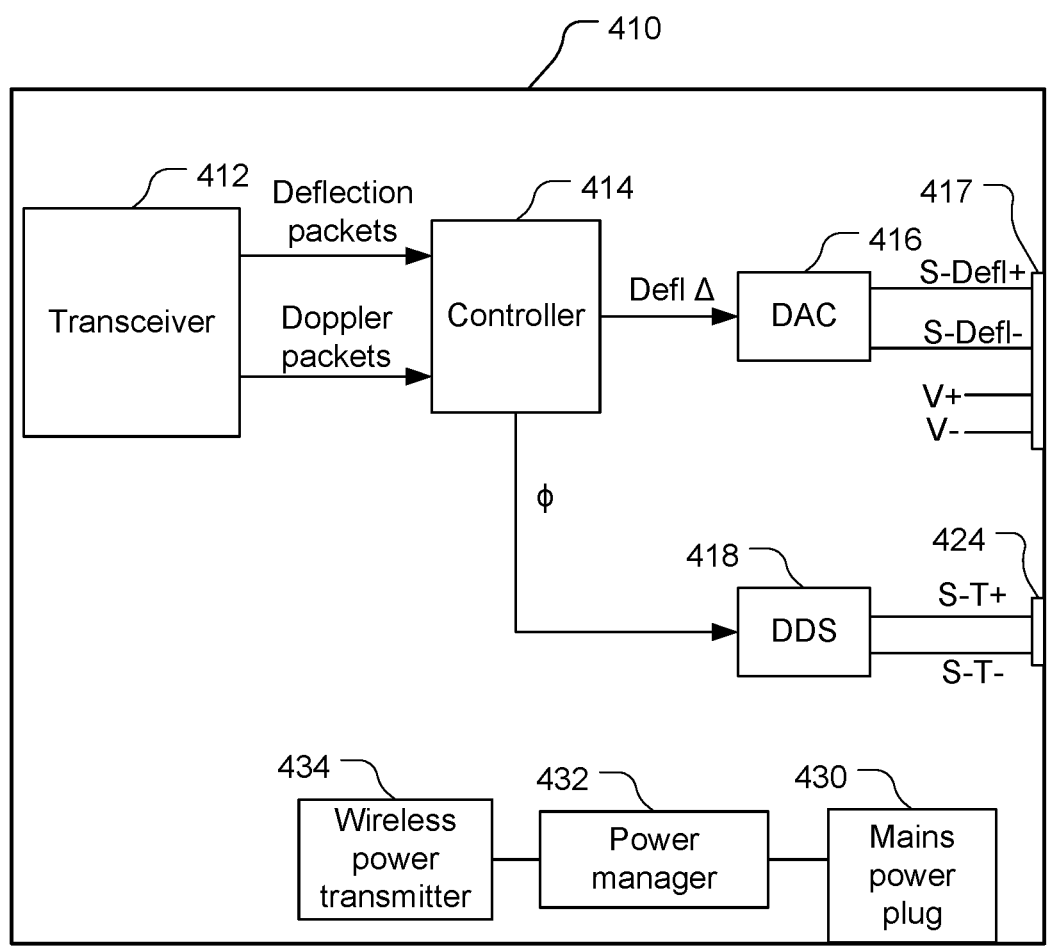
FIG. 10 is a simplified schematic of components of an example of a base station shown in FIG. 7.

Referring to FIG. 10, with further reference to FIGS. 1-9, an example of a base station 410, which may be an example of the base station 14 shown in FIG. 3, the base station 14 shown in FIG. 4, the base station 114 shown in FIG. 6, or the base station 124 shown in FIG. 7, includes the components shown. The components shown in FIG. 10 are coupled to each other as shown by lines between the components, with arrows on respective lines indicating directions of signal flow. The base station 410 in this example is configured to receive digital wireless communications from the CTG system 210 and the TOCO 310, and to produce analog signals expected by the wired monitor 504 to process and display indications of uterine contractions and fetal heartbeat. The base station 410 includes a transceiver 412 configured to receive packets of information (Doppler packets and deflection packets) from the CTG system 210 and the TOCO 310 indicative of fetal heartbeat and uterine contractions, respectively. The transceiver 412 is configured to provide the deflection packets and the Doppler packets, containing information regarding the uterine contractions and the fetal heartbeat, respectively, to a controller 414.

The controller 414 is configured to process the deflection packets from the transceiver 412 to provide an indication of the voltage difference between the Defl+ and Defl− signals output by the bridge 320. The controller 414 provides a deflection difference signal Defl Δ, indicative of the difference between the strain voltages, to a digital-two-analog converter (DAC) 416.

The DAC 416 is configured to convert the digital indication of the difference in strain voltages into analog voltages as synthetic deflection signals S-Defl+, S-Defl− that are attempted reproductions of the deflection signals produced by the bridge 320. The synthetic deflection signals S-Defl+, S-Defl− output by the DAC 416 may not be identical to the deflection signals Defl+, Defl− output by the bridge 320, but will be similar, and will have a voltage difference that is close to, if not the same as, the voltage difference of the deflection signals Defl+, Defl− output by the bridge 320.

The base station 410 further includes reference voltage lines for reference voltages V+, V− that may be provided at a single connector 417, along with Defl+ and Defl− lines, that may be connected to a cable that is configured to connect to the monitor 504 to provide the Defl+, Defl−, V+, and V− signals to the monitor 504 as though the TOCO 310 was hard wired to the monitor 504.

A direct digital synthesizer (DDS) 418 includes a portion of the controller 414 and is configured to attempt to produce synthetic transducer signals S-T+, S-T− that are attempted reproductions of the transducer signals T+, T− produced by the piezoelectric element 224 in the electrodes 220, 222. The controller 414 is configured to receive Doppler packets from the transceiver 412 indicating the phase shift ϕ of the inbound US signals 228 and provide indications of these phase shifts from the payloads of the Doppler packets to the DDS 418. The DDS 418 is configured to convert the digital indications of the phase shifts into analog signals using information regarding the frequency modulation (i.e., the Doppler frequency shift due to the fetal heart beat) to produce synthesized Transducer-positive and synthesized Transducer-negative signals S-T+, S-T− that are attempts at reproductions of the transducer signals T+, T− produced by the piezoelectric element 224 in the electrodes 220, 222. The base station 410 further includes a connector 424 that may be connected to a shielded cable that is configured to connect to the monitor 504 to provide the synthetic signals S-T+, S-T− to the monitor 504 as though the CTG system 210 was hard-wired to the monitor 504.

The base station 410 further includes a mains power plug 430, a power manager 432, and a wireless power transmitter 434. The mains power plug 430 is configured to connect to a cable that is configured to connect to a wall outlet for receiving mains power. The wireless power transmitter 434 is configured to transmit power wirelessly. The wireless power receiver 254 may be, for example, a coil configured to produce to a magnetic field to couple to the wireless power receiver 254, a plate configured to couple power capacitively couple to the wireless power receiver 254, etc. The power manager 432 is configured to use energy received via the mains power plug 430 to provide power to components of the base station 410, to provide the reference voltages V+, V−, and to provide power to the wireless power transmitter 434.

The power manager 432 may be configured to provide one or more instructions to the wireless power transmitter, or to the controller 414, to be conveyed by a magnetic field produced by the transmitter 434, or sent via the transceiver 412, to the CTG system 210 and/or to the TOCO 310. For example, the base station 410 may send an instruction to the TOCO 310 to initiate calibration of the bridge 320. As another example, the base station 410 may send an instruction to the TOCO 310 to adjust the variable resistor 328 by a specified amount in order to calibrate the bridge 320. This instruction may be sent by the transceiver 412 from the controller 414, or via the wireless power transmitter 434 from the power manager 432 (e.g., by altering a magnetic field produced by the transmitter 434). For example, the calibration instruction for the TOCO 310 may be sent in response to detection that the wireless power receiver 254 is in close proximity to the wireless power transmitter 434, e.g., by detection of a change in impedance of the transmitter 434, by detection of triggering of a mechanical switch indicating that the sensor 12 is docked to the base station 410. As another example, the calibration instruction may be sent to the TOCO 310 in response to a determination that the wireless power receiver 254 is receiving power from the wireless power transmitter 434, as communicated to the base station 410 from the TOCO 310. As another example, the base station 410 may send instructions (e.g., via the transceiver 412 from the controller 414) to the CTG system 210 to transmit the outbound US signals 226 (e.g., to regulate the sending of the gate signal and/or the T/R signal by the controller 216). The power manager 432 may be comprised, at least partially, by the controller 414 or be communicatively coupled to the controller 414, e.g., to supply communication signals received from the controller 414 to the wireless power transmitter 434.

Figure 11:
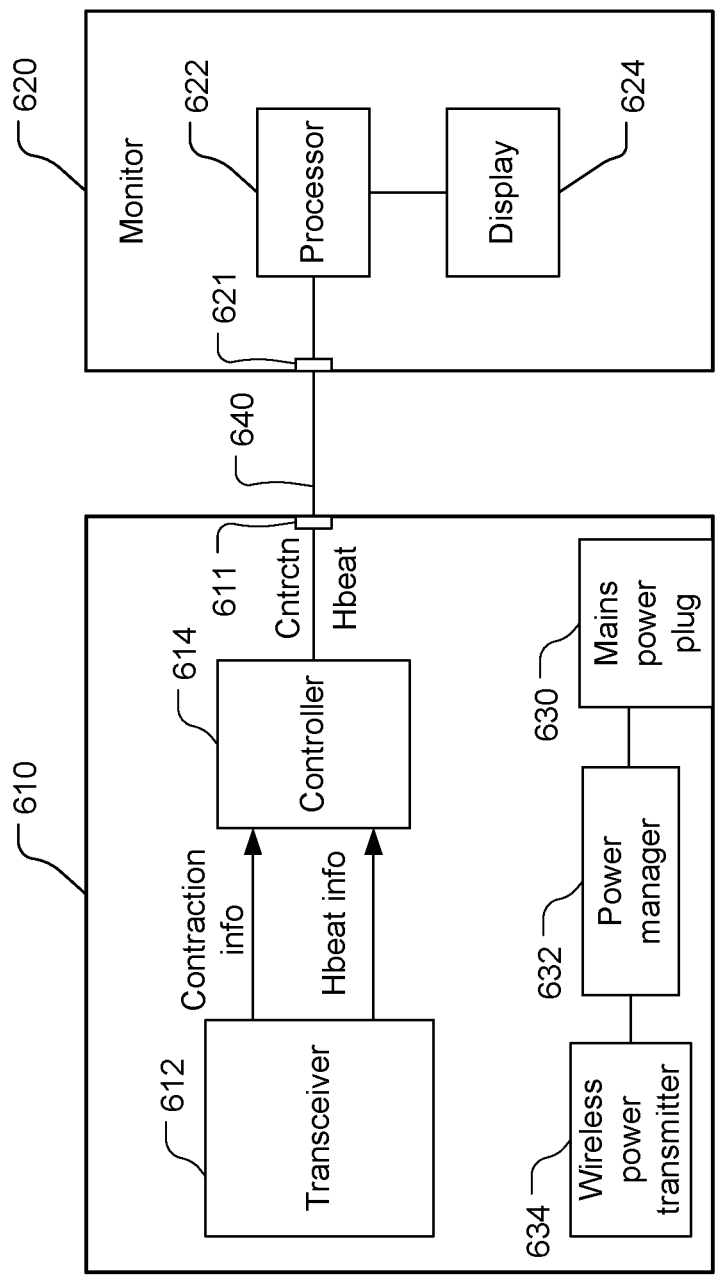
FIG. 11 is a block diagram of another example of the base station shown in FIG. 7, and a monitor.

Referring to FIG. 11, with further reference to FIGS. 1-10, an example of a base station 610, which may be another example of the base station 14 shown in FIG. 3, the base station 14 shown in FIG. 4, the base station 114 shown in FIG. 6, or the base station 124 shown in FIG. 7, is connected to an example of a monitor 620. The base station 610 and the monitor 620 include the components shown. The components shown in FIG. 11 are coupled to each other as shown by lines between the components, with arrows on respective lines indicating directions of signal flow. The base station 610 in this example is configured to receive digital wireless communications from the CTG system 210 and the TOCO 310, and to provide digital signals expected by the wired monitor 504 to process and display indications of uterine contractions and fetal heartbeat. The base station 610 includes a transceiver 612 configured to receive information (e.g., Doppler packets and deflection packets) from the CTG system 210 and the TOCO 310 indicative of fetal heartbeat and uterine contractions, respectively. The transceiver 612 is configured to provide the contraction information and the heartbeat information to a controller 614.

The controller 614 may be configured to provide a contraction output signal Cntrctn, to a connector 611, based on the contraction information received from the transceiver 612. The contraction output signal Cntrctn is indicative of the contraction information received from the transceiver 612, and may include an analog signal as discussed above (e.g., with the controller 614 including the controller 414 and the DAC 416 discussed with respect to FIG. 10) and/or a digital signal as discussed below. The contraction output signal Cntrctn may indicate values of the deflection signals Defl+, Defl− received by the transceiver 612, i.e., raw information from which severity of a contraction can be determined by the monitor 620. Also or alternatively, the contraction output signal Cntrctn may be an indication of the contraction itself. That is, the controller 614 may be configured to convert the indications of values of the deflection signals Defl+, Defl− (and/or other contraction information from the transceiver 612) to indications of contraction strength and possibly contraction trend (e.g., contracting (strengthening), relaxing (weakening)).

The controller 614 may be configured to provide a heartbeat output signal Hbeat, to the connector 611, based on the heartbeat information received from the transceiver 612. The heartbeat output signal Hbeat is indicative of the heartbeat information received from the transceiver 612, and may include an analog signal as discussed above (e.g., with the controller 614 including the controller 414 and the DDS 418 discussed with respect to FIG. 10) and/or a digital signal as discussed below. The heartbeat output signal Hbeat may indicate values of the transducer signals T+, T− received by the transceiver 612, i.e., raw information from which severity of a contraction can be determined by the monitor 620. Also or alternatively, the heartbeat output signal Hbeat may indicate a heart rate (e.g., a number of beats per minute). That is, the controller 614 may be configured to analyze the heartbeat information from the transceiver 612 to determine the heart rate and provide the heart rate in the heartbeat output signal Hbeat.

The functionality of analyzing contraction information and/or the heartbeat information may be performed outside of the base station 610. For example, the functionality of analyzing contraction information (e.g., deflection signal values) to determine biological function (e.g., contraction severity and/or trend) may be performed in a TOCO, e.g., in the controller 334 of the TOCO 310. In this case, the contraction information may indicate the biological function and be sent by the TOCO 310 to the base station 610. Also or alternatively, analysis of contraction information such as the deflection signal values may be performed by the wired monitor 620, e.g., a processor 622 of the wired monitor 620. Also or alternatively, the functionality of analyzing heartbeat information to determine heart rate may be performed in a CTG system, e.g., in the controller 216 of the CTG system 210. In this case, the heartbeat information may indicate the heart rate and be sent by the CTG system 210 to the base station 610. Also or alternatively, analysis of heartbeat information such as the transducer signal values may be performed by the wired monitor 620, e.g., the processor 622 of the wired monitor 620.

The controller 614 is configured to provide the contraction output signal Cntrctn and the heartbeat output signal Hbeat according to one or more appropriate protocols. For example, the controller 614 may produce the contraction output signal Cntrctn and the heartbeat output signal Hbeat according to a digital communication standard such as the UART (Universal Asynchronous Receiver-Transmitter) protocol or the SPI (Serial Peripheral Interface) protocol, or another communication standard protocol, or a non-standard communication protocol.

The base station 610 further includes a mains power plug 630, a power manager 632, and a wireless power transmitter 634 that may be configured similarly to the mains power plug 430, a power manager 432, and a wireless power transmitter 434 discussed above. The connector 611, similar to the connector 417, is configured to connect to a wire 640 that can be connected to the monitor 620.

The monitor 620 is configured to receive signals, via a connector 621, and to process the received contraction output signal and the heartbeat output signal and display corresponding information to a user. For example, the processor 622 may use a stored map of deflection signal values (or difference in deflection signal values, or other information in the contraction output signal Cntrctn) to values expected by a display 624 such that the display 624 will display an appropriate, corresponding indication of the contraction. Similarly, the processor 622 may use a stored map of transducer signal values (or other information in the heartbeat output signal Hbeat) to values expected by the display 624 such that the display 624 will display an appropriate, corresponding indication of the heartbeat, e.g., heart rate. Also or alternatively, the monitor 620 may include some or all of the functionality of the base station 610, e.g., such that the monitor may receive wireless communications from a CTG system, such as the CTG system 210, or from a TOCO, such as the TOCO 310, directly.

Figure 12:
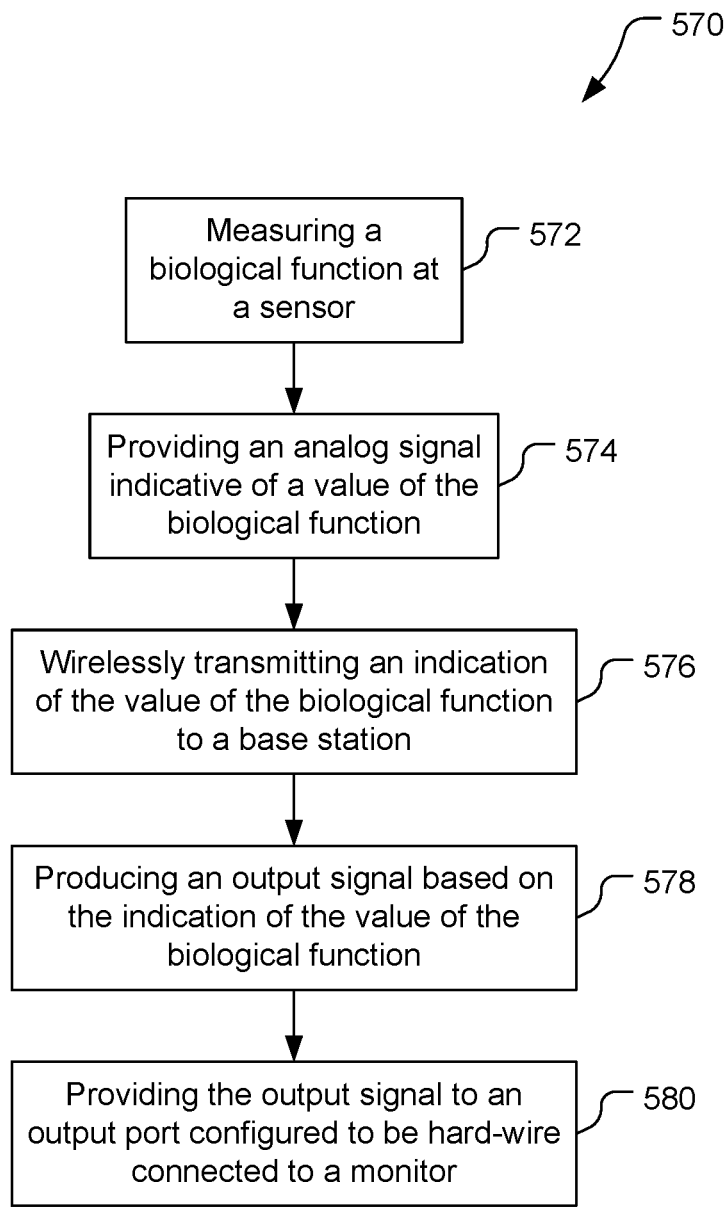
FIG. 12 is a block flow diagram of a biological function sensing and reporting method.

Referring to FIG. 12, with further reference to FIGS. 3-11, a biological function sensing and reporting method 570 includes the stages shown. The method 570 is, however, an example only and not limiting. The method 570 may be altered, e.g., by having stages added, removed, rearranged, combined, performed concurrently, and/or having single stages split into multiple stages.

At stage 572, the method 570 includes measuring a biological function at a sensor. For example, the sensor 12 (e.g., the CTG system 210 and/or the TOCO 310) measures a biological function such as a fetal heartbeat and/or a uterine contraction.

At stage 574, the method 570 includes providing an analog signal indicative of a value of the biological function. For example, the piezoelectric element 224, and the electrodes 220, 222 produce the transducer signals T+, T− indicative of fetal heart movement. As another example, the bridge 320, in conjunction with the strain gauges 312, 314, produce the Defl+ and Defl− signals indicative of a uterine contraction.

At stage 576, the method 570 includes wirelessly transmitting an indication of the value of the biological function to a base station. For example, the transceiver 246 transmits a packet of information indicating values of multiple samples of the transducer signals T+, T− to the base station 410. As another example, the transceiver 246 may transmit a digital signal as indicative of a heart rate, e.g., a numerical value of heart rate (e.g., numbers of beats per minute). As another example, the transceiver 336 sends one or more packets indicating one or more values of each of the Defl+ and Defl− signals, or one or more values of a difference between the Defl+ and Defl− signals, to the base station 410. As another example, the transceiver 336 may send a digital signal indicative of a contraction, e.g., strength and trend of the contraction.

At stage 578, the method 570 includes producing an output signal based on the indication of the value of the biological function. For example, the base station 410 may produce the synthetic analog deflection signals S-Defl+, S-Defl− as attempted replicas of the deflection signals Defl+, Defl− produced by the bridge 320. As another example, the base station 410 may produce the synthetic analog transducer signals S-T+, S-T− as attempted replicas of the transducer signals T+, T− produced by the piezoelectric element 224 and the electrodes 220, 222. As other examples, the base station 610 may produce and send one or more digital signals indicative of deflection values, transducer signal values, contraction intensity, contraction trend, and/or heart rate, etc.

At stage 580, the method 570 includes providing the second analog signal to an output port configured to be hard-wire connected to a monitor. For example, the synthetic deflection signals S-Defl+, S-Defl− may be provided to the connector 417 and/or the synthetic transducer signals S-T+, S-T− may be provided to the connector 424, with each of the connectors 417, 424 configured to be hard-wire connected to the monitor 504. As other examples, the contraction output signal Cntrctn and/or the heartbeat output signal Hbeat may be provided to the connector 611, and thus to the monitor 620 via the wire 640 and the connector 621. The method 570 may further include the monitor 504 displaying a visual indication of the value of the biological function on a display of the monitor. For example, the display 562 may show one or more visual indications of the fetal heart movement (e.g., a contraction intensity over time) and/or of a uterine contraction (e.g., a contraction intensity over time).

Figure 13:
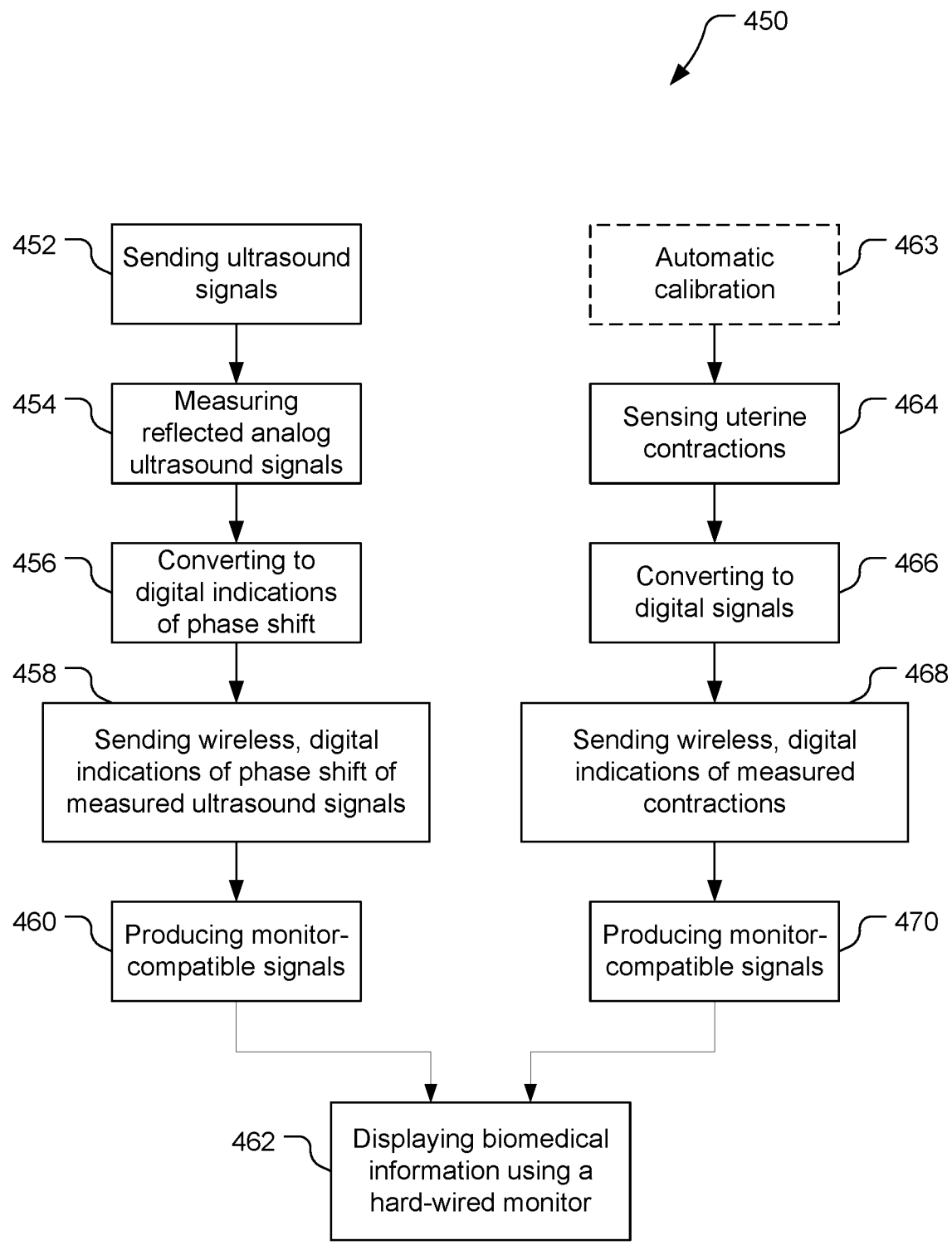
FIG. 13 is a block flow diagram of a method of sensing and reporting biomedical information.

Referring to FIG. 13, with further reference to FIGS. 3-12, a method 450 of sensing and reporting biomedical information includes the stages shown. The method 450 is an example of the method 570 shown in FIG. 12. The method 450 includes transferring the biomedical information wirelessly, and displaying indications of the biomedical information using a legacy, hard-wired monitor. The method 450 is, however, an example only and not limiting. The method 450 may be altered, e.g., by having stages added, removed, rearranged, combined, performed concurrently, and/or having single stages split into multiple stages. For example, one or more of stages 452, 454, 456, 458, 460 may be performed concurrently with one or more of stages 464, 466, 468, 470. Further, while stages 464, 466, 468, 470 are discussed with respect to uterine contractions, other biomedical information may be sensed and processed, e.g., for display.

At stage 452, the method 450 includes sending ultrasound signals. For example, the controller 216 sends the gate signal to the transmission amplifier 214 to allow the clock signal CLK from the clock 212 to be transferred to the T/R switch 218. The controller 216 also sends the T/R signal to the T/R switch rural 218 such that the T/R switching 218 transfers the drive signal to the electrodes 220, 222 to excite the piezoelectric element 224 to produce the outbound US signals 226. The controller 216 may send the gate signal in response to receiving an instruction to do so via the transceiver 246 from the base station 410. The controller 216, for example, controls the production and transmission of the outbound US signals 226 such that the outbound US signals 226 are conveyed in bursts. Each of the bursts are, for example, composed of the drive signal with a frequency of 1.151 MHz, having a duration of, e.g., 150 μs, and with multiple bursts having a repetition rate of 4 KHz (i.e., a new burst being sent every 250 μs).

At stage 454, the method 450 includes measuring reflected analog ultrasound signals. For example, the inbound US signals 228 are received by the piezoelectric element 224, converted to electrical signals T+, T− by the electrodes 220, 222 and provided to the T/R switch 218. The controller 216 provides the T/R signal to the T/R switch 218 such that the T/R switch 218 converts the T+ and T− signals to a CTG signal and provides the CTG signal to the receive amplifier 230. The CTG signal indicates the phase shift (i.e., Doppler frequency) of the inbound US signals 228.

At stage 456, the method 450 includes converting to digital indications of faith shift. For example, the amplified CTG signal is provided by the receive amplifier 232 the I and Q mixers 234, 236 (via the phase shifter 232 for the mixer 234) for quadrature separation and processing. The mixers 234, 236 downconvert the I and Q signals and the LPFs 238, 240 and the ADCs 242, 244 filter and convert the I and Q signals to digital signals that are provided to the controller 216.

At stage 458, the method 450 includes sending wireless, digital indications of a shift of measured ultrasound signals. For example, the controller 216 compiles a packet of information including multiple measurements of the inbound US signals 228 and sends the packet to the transceiver 246 that wirelessly transmits the packet to the base station 410 via an appropriate wireless protocol.

At stage 460, the method 450 includes producing monitor-compatible signals. The monitor-compatible signals are in a format expected by the monitor and can be used to display information to a user regarding the uterine contractions. The monitor-compatible signals may include digital signals and/or analog signals. For example, the monitor-compatible signals may include digital indications of ultrasound transducer output values, or indications of heart rate, etc. Also or alternatively, the monitor-compatible signals may include analog signals that are attempted reproductions of the transducer signals T+, T−. For example, the transceiver 412 receives the packet of information indicating the phase shifts of the inbound US signals 228 for the samples contained within the packet. The transceiver 412 supplies Doppler packet to the controller 414 that extracts the phase information from the packet and provides the phase information to the DDS 418. While FIG. 10 shows Doppler packets, plural, being provided from the transceiver 412 to the controller 414, a single packet may be provided at a time, with multiple packets being provided over time. The DDS 418 converts the phase information to the Synthetic-Tranducer-positive signal S-T+ and the Synthetic-Transducer-negative signal S-T− that are approximate reproductions of the transducer signals T+, T− produced by the piezoelectric element 224 in response to receiving the inbound US signals 228.

At stage 462, the method 450 includes displaying biomedical information using a legacy, hard-wired monitor. For example, the monitor 504 receives the analog signals from the base station 410 that are indicative of the inbound US signals 228, processes these signals in the signal processor 564 as appropriate, and displays indications of the biomedical information, e.g., fetal heartbeat, on the display 562.

At optional stage 463, the method 450 includes automatic calibration. For example, the TOCO 310 may be automatically calibrated as discussed above, e.g., in response to docking of the TOCO 310 with the base station 14, the TOCO 310 coming in close proximity to the base station 14, and/or the TOCO 310 being charged by the base station 14, and/or in response to one or more other conditions being met. While the stage 463 is shown as being performed before the stage 464, the stage 463 may be performed at other times in the method 450. Further, the stage 463 may be performed in the method 570 shown in FIG. 12, even if one or more other stages of the method 450 are not performed.

At stage 464, the method 450 includes sensing uterine contractions. For example, the strain gauges 312, 314 may sense strains, or deflections, of the flexible sheet 316 and provide corresponding resistances as the resistors 322, 324. Voltages produced by the bridge 320 as the Defl+ and Defl− signals are provided by the bridge 320 as indications of the strains put on the flexible sheet 316 which are indicative of a uterine contraction.

At stage 466, the method 450 includes converting to digital signals. For example, the Defl+ and Defl− signals are provided to the amplifier 330 and from there to the ADC 332 for converting the signals indicating one or more characteristics, e.g., magnitude, of the uterine contraction from the analog Defl+ and Defl− signals to digital indications of these signals.

At stage 468, the method 450 includes sending wireless, digital indications of measured contractions. For example, the controller 334 may collect the information regarding the Defl+ and Defl− signals and format the information into a packet that the controller 334 provides to the transceiver 336. The transceiver 336 sends the packet indicating the information regarding the Defl+ and Defl− signals (e.g., a value of each of the Defl+ and Defl− signals, or a difference between the Defl+ and Defl− signals, etc.) to the base station 410.

At stage 470, the method 450 includes producing monitor-compatible signals. The monitor-compatible signals are in a format expected by the monitor and can be used to display information to a user regarding the uterine contractions. The monitor-compatible signals may include digital signals and/or analog signals. For example, the monitor-compatible signals may include digital indications of deflection signal values, or indications of contraction strength and/or trend, etc. Also or alternatively, the monitor-compatible signals may include analog signals that are attempted reproductions of the deflection signals Defl+, Defl−. For example, the transceiver 412 receives the packet indicating the values of the Defl+ and Defl− signals and provides the packet to the controller 414. While FIG. 10 shows deflection packets, plural, being provided from the transceiver 412 to the controller 414, a single packet may be provided at a time, with multiple packets being provided over time. The controller 414 extracts the information regarding the Defl+ and Defl− signal and provides an indication of the values of the Defl+ and Defl− signals, or a value of a difference of the Defl+ and Defl− signals, to the DAC 416. The DAC 416 converts the received digital information into the Synthetic-Defl+ and Synthetic-Defl− signals that are approximate reproductions of the deflection signals Defl+, Defl− produced by the bridge 320 in response to deflection of the flexible sheet 316 as measured by the strain gauges 312, 314. The base station 410 provides the synthetic Defl+ and Defl− signals to the connector 417 that is to be connected to the monitor 504.

At stage 462, the method 450 again includes displaying biomedical information using the legacy, hard-wired monitor. For example, the monitor 504 receives the synthetic deflection signals S-Defl+, S-Defl− and the reference voltages V+ and V−, amplifies the S-Defl+ and S-Defl− signals using the amplifier 560, and displays indications of the uterine contraction using the displayed 562. Thus, the monitor 504 may use the synthetic deflection signals S-Defl+, S-Defl−, that are nearly identical to the Defl+ and Defl− signals produced by the bridge 320, to display information regarding uterine contractions, and may use the synthetic transducer signals S-T+, S-T−, that are nearly identical to the T− and T+ signals produced by the piezoelectric element 224 and the electrodes 220, 222, to display information regarding fetal heartbeat (or movement of other items reflecting the outbound US signals 226).

Other Considerations

Various alternative to the configurations discussed may be used. For example, a voice coil may be used instead of the Wheatstone bridge 320, with the voice coil including a coil and a current supply (e.g., an amplifier). The voice coil may be automatically calibrated (e.g., in response to one or more triggers discussed above) by adjusting a current provided to the coil (e.g., by adjusting a gain of the amplifier providing current to the coil) under no-load and known-load conditions to achieve desired output measurements. The values for the input current (e.g., the amplifier gain values) may be used by the controller 334 to determine a relationship of deflection-to-load (corresponding to deflection-to-intensity of a uterine contraction) using the no-load current value and the loaded current value.

Also, as used herein, "or" as used in a list of items prefaced by "at least one of" or prefaced by "one or more of" indicates a disjunctive list such that, for example, a list of "at least one of A, B, or C," or a list of "one or more of A, B, or C" means A or B or C or AB or AC or BC or ABC (i.e., A and B and C), or combinations with more than one feature (e.g., AA, AAB, ABBC, etc.).

Further, an indication that information is sent or transmitted, or a statement of sending or transmitting information, "to" an entity does not require completion of the communication. Such indications or statements include situations where the information is conveyed from a sending entity but does not reach an intended recipient of the information. The intended recipient, even if not actually receiving the information, may still be referred to as a receiving entity, e.g., a receiving execution environment. Further, an entity that is configured to send or transmit information "to" an intended recipient is not required to be configured to complete the delivery of the information to the intended recipient. For example, the entity may provide the information, with an indication of the intended recipient, to another entity that is capable of forwarding the information along with an indication of the intended recipient.

Substantial variations may be made in accordance with specific requirements. For example, customized hardware might also be used, and/or particular elements might be implemented in hardware, software (including portable software, such as applets, etc.) executed by a processor, or both. Further, connection to other computing devices such as network input/output devices may be employed.

The systems and devices discussed above are examples. Various configurations may omit, substitute, or add various procedures or components as appropriate. For instance, features described with respect to certain configurations may be combined in various other configurations. Different aspects and elements of the configurations may be combined in a similar manner. Also, technology evolves and, thus, many of the elements are examples and do not limit the scope of the disclosure or claims.

A wireless communication system is one in which at least some communications are conveyed wirelessly, e.g., by electromagnetic and/or acoustic waves propagating through atmospheric space rather than through a wire or other physical connection. A wireless communication network may not have all communications transmitted wirelessly, but is configured to have at least some communications transmitted wirelessly. Further, the term "wireless communication device," or similar term, does not require that the functionality of the device is exclusively, or evenly primarily, for communication, or that the device be a mobile device, but indicates that the device includes wireless communication capability (one-way or two-way), e.g., includes at least one radio (each radio being part of a transmitter, receiver, or transceiver) for wireless communication.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of operations may be undertaken before, during, or after the above elements are considered. Accordingly, the above description does not bound the scope of the claims.

Further, more than one invention may be disclosed.

The invention claimed is:

1. A patient monitoring system comprising:
    a biomedical sensor configured to be attached to a patient and comprising:
        a sensor processor;
        a sensor transceiver communicatively coupled to the sensor processor; and
        a measurement unit comprising
            a tocodynamometer configured to sense uterine contractions and provide uterine contraction information;
        the sensor transceiver being communicatively coupled to the measurement unit and configured to transmit, wirelessly, biomedical monitoring signals indicative of the uterine contraction information; and
    a base station including:
        a base station transceiver; and
        a base station processor communicatively coupled to the base station transceiver and configured to:
            communicate wirelessly with the sensor processor via the base station transceiver and the sensor transceiver to establish a wireless communication arrangement between the biomedical sensor and the base station to inhibit devices other than the base station from determining the uterine contraction information from the biomedical monitoring signals; and
            send a calibration signal to the biomedical sensor to cause the biomedical sensor to calibrate the tocodynamometer, the base station processor being configured to send the calibration signal in response to the biomedical sensor coming in close proximity to the base station, or the biomedical sensor being docked with the base station, or a combination thereof.

2. The system of claim 1, wherein the base station processor is configured to initiate establishment of the wireless communication arrangement in response to the biomedical sensor coming in close proximity to the base station, or the base station processor is configured to initiate establishment of the wireless communication arrangement in response to the biomedical sensor being docked with the base station, or a combination thereof.

3. The system of claim 2, wherein the base station processor is configured to communicate with the sensor processor according to the wireless communication arrangement until the biomedical sensor leaves close proximity to the base station and either the biomedical sensor or another biomedical sensor comes in close proximity to the base station, or the base station processor is configured to communicate with the sensor processor according to the wireless communication arrangement until the biomedical sensor is de-docked from the base station and either the biomedical sensor or another biomedical sensor is docked with the base station, or a combination thereof.

4. The system of claim 1, wherein the measurement unit further comprises an ultrasound unit configured to sense a fetal heartbeat and provide fetal heartbeat information, the biomedical monitoring signals are further indicative of the fetal heartbeat information, and the base station processor is further configured to establish the wireless communication arrangement between the biomedical sensor and the base station to inhibit devices other than the base station from determining the fetal heartbeat information.

* * * * *